(12) United States Patent
Amundson et al.

(10) Patent No.: US 6,178,346 B1
(45) Date of Patent: Jan. 23, 2001

(54) INFRARED ENDOSCOPIC IMAGING IN A LIQUID WITH SUSPENDED PARTICLES: METHOD AND APPARATUS

(76) Inventors: David C. Amundson, 249 Spruce St., Boulder, CO (US) 80302; H. John Hanlin, 874 W. Barberry Cir., Louisville, CO (US) 80027

( * ) Notice: Under 35 U.S.C. 154(b), the term of this patent shall be extended for 0 days.

(21) Appl. No.: 09/178,566

(22) Filed: Oct. 23, 1998

(51) Int. Cl.⁷ ..................................... A61B 5/00
(52) U.S. Cl. ............... 600/473; 600/160; 600/342; 348/77
(58) Field of Search ................... 600/473, 310, 600/342, 109, 160, 178, 478; 606/2–4, 15; 348/65, 67, 68, 77, 78; 356/39, 43, 51

(56) References Cited

U.S. PATENT DOCUMENTS

| | | |
|---|---|---|
| 3,938,502 | 2/1976 | Bom . |
| 4,224,929 | 9/1980 | Furihata . |
| 4,418,689 | 12/1983 | Kanazawa . |
| 4,470,407 | 9/1984 | Hussein . |
| 4,539,588 | 9/1985 | Ariessohn . |
| 4,621,284 * | 11/1986 | Nishioka et al. ............. 358/98 |
| 4,685,451 * | 8/1987 | Ando ........................... 128/6 |
| 4,917,097 | 4/1990 | Proudian . |
| 5,147,354 | 9/1992 | Boutacoff . |
| 5,400,791 * | 3/1995 | Schlier et al. ................ 128/664 |
| 5,445,157 * | 8/1995 | Adachi et al. ................ 128/664 |
| 5,517,997 * | 5/1996 | Fontenot ...................... 128/664 |
| 5,690,605 * | 11/1997 | Hamlin et al. ............... 600/109 |
| 5,769,076 * | 6/1998 | Maekawa et al. ............ 128/633 |
| 5,865,829 * | 2/1999 | Kitajima ...................... 606/3 |
| 5,876,121 * | 3/1999 | Burns et al. ................. 374/161 |
| 5,879,306 * | 3/1999 | Fontenot et al. ............ 600/473 |
| 5,919,132 * | 7/1999 | Faubert et al. ............. 600/318 |
| 5,931,789 * | 8/1999 | Alfano et al. ............... 600/473 |
| 5,983,120 * | 11/1999 | Groner et al. .............. 600/310 |
| 5,997,472 * | 12/1999 | Bonnell et al. ............. 600/109 |

* cited by examiner

*Primary Examiner*—Marvin M. Lateef
*Assistant Examiner*—Shawna J. Shaw
(74) *Attorney, Agent, or Firm*—Gibson, Dunn & Crutcher LLP

(57) ABSTRACT

A device and method for imaging an object that is situated within a fluid environment having suspended particles uses infrared illumination. In a representative application, a catheter having fiber optics is inserted into the vasculature of a patient. The fiber optics transmits infrared light to an optical head at a distal end of the catheter, which transmits the light into a bloody environment to an object to be imaged. Light reflecting from the object is collected and transmitted throughout the fiber optic to an infrared camera, so that an image is formed. Proper selection of the wavelength of infrared illumination allows objects to be imaged through what would otherwise be an opaque liquid. The invention has particular utility in the field of medical imaging.

62 Claims, 16 Drawing Sheets

Electromagnetic Spectrum

Absorption of Water & Hemoglobin

Normalized Scattering Cross-section versus q = 6.28 x radius / wavelength q = 6.28 x radius / wavelength Refractive Index Effects on Q(ref ind, ref ind delta)

Shape of Red Blood Cell

Normalized Scattering Cross-section for Blood versus Wavelength

Viewing Distance through Blood versus Wavelength

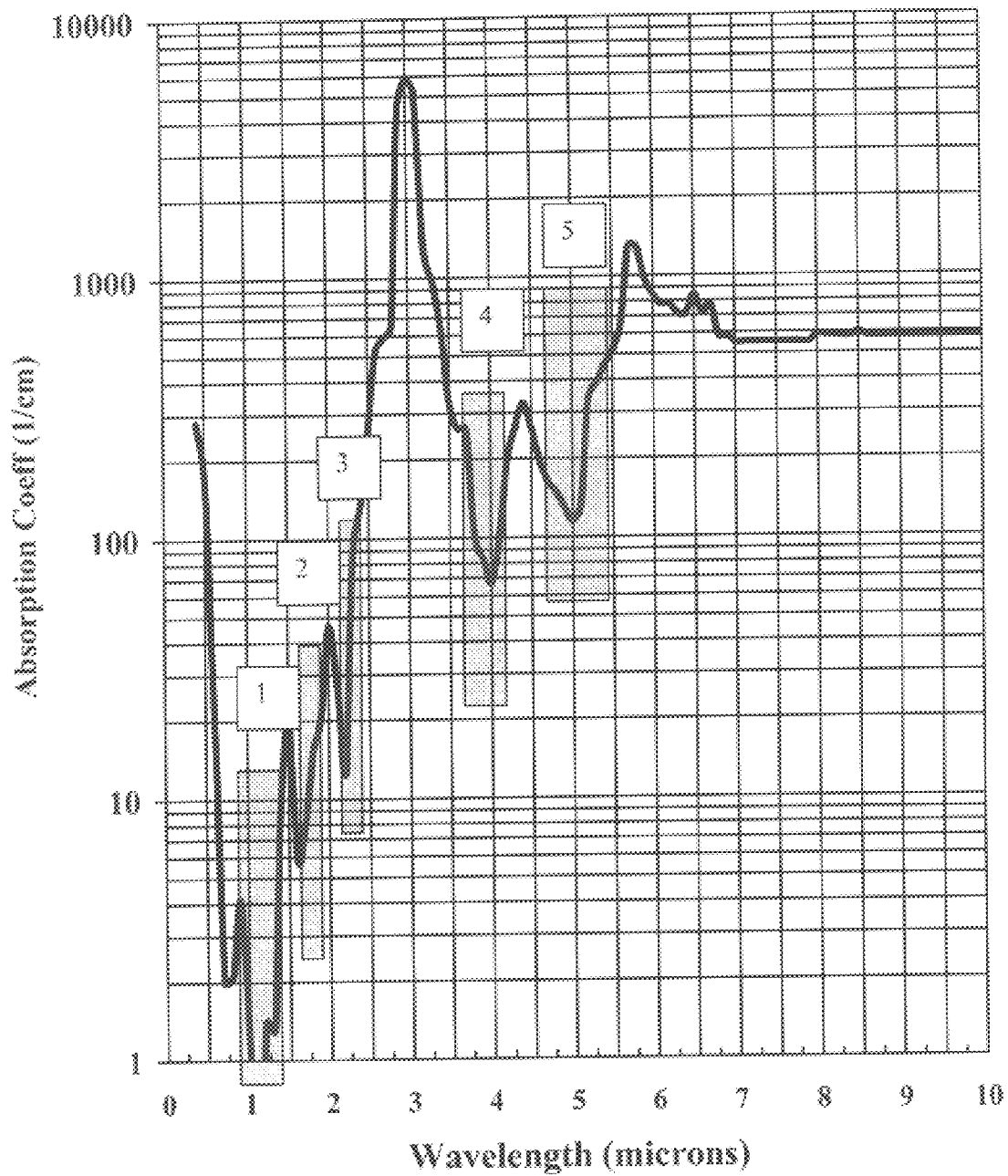

INFRARED ENDOSCOPIC IMAGING IN A LIQUID WITH SUSPENDED PARTICLES: METHOD AND APPARATUS

FIELD OF INVENTION

This invention relates to the endoscopic imaging of structures in a liquid with suspended particles, such as blood, and apparatus for accomplishing such imaging.

BACKGROUND

Heart disease is the number one killer in the U.S. and many other countries. In the United States, heart disease results in the death of almost one million people per year. The high mortality and morbidity rate has led to many drug and device therapies to intervene in the progression of heart disease. Aggressive therapy for many forms of heart disease involve interventions where a cardiologist inserts a catheter in the patients artery or vein and performs procedures such as angioplasty, pacemaker or implantable defibrillator lead insertion or electrical mapping. These procedures have grown dramatically on a cost-basis: 947 million dollars were spent in 1990 vs.4.6 billion dollars spent in 1996.

Interventional procedures in cardiology are all the more remarkable since these procedures are performed only under radiographic guidance. Radiography presents the physician with a faint outline of the heart and its relation to the catheter. While radiography provides the cardiologist a crude guide, it does not allow examination of surfaces of the heart and vasculature or provide enough vision to guide procedures such as angioplasty or ablation.

In other body cavities, not filled with blood, such as the stomach or esophagus, fluid can be evacuated permitting visible wavelengths to be used in endoscope imaging. Visualizing the structure allows minimally invasive procedures such as ablating, stapling and suturing to be performed. These procedures, called laparoscopic procedures, are guided by the insertion of an endoscope, permitting visual examination of the treatment. These procedures are done in a saline bath or air to permit clear viewing. For example, minimally invasive orthopedic procedures rely on the endoscopic image to guide treatment. It is unfortunate cardiology has not had access to this technology since the common procedures would benefit from visualization.

The advantages to seeing structures in the cardiovascular system are numerous. Current methods of visualizing structures in the cardiovascular system are limited to radiography, ultrasound and angioscopy. Radiography is the standard visual tool used to image interventional cardiology procedures. It is applied by a large X-ray apparatus on a C-arm that will rotate around the patient through 180 degrees. The heart appears as a faint outline; while the metallic catheters are brightest. This allows for gross estimation of the catheter end to faint landmarks of the heart. The C-arm is frequently repositioned to give better viewing perspectives. Once the catheter has been navigated to the heart it can be placed in a coronary artery. In a self-contained entity such as an artery or vein, flouroscopic sensitive dye can be injected out the distal end of the catheter and viewed on the radiography camera for a short distance before it diffuses with blood. This technique is used to spot constricted areas in the coronary arteries. It has been shown that radiography, however, usually underestimates the degree of stenosis and therefore is only useful in providing a gross measure of flow.

More accurate assessments of coronary flow have been pioneered in the coronary arteries to evaluate angioplasty treatment. In the vasculature, the current angioplasty procedure for revascularization of an occluded coronary artery is to insert a catheter in the arterial tree, select the appropriate coronary artery, place an expandable balloon across the lesion and apply external pressure. As the pressure is reduced an expandable metallic structure (stent) remains opened to provide a scaffold, preventing the coronary artery from closing. This procedure is only effective long-term about 75–80% of the time. It is thought that many of these restenosis are due to inappropriate pressure application or inadequate stent placement. Oftentimes, postmortems have revealed stent buckling which can obstruct the flow rate in the coronary artery.

This information is so important, a form of endoscopy for the coronary arteries has been developed; called angioscopy. Examples of the art are contained in U.S. Patents since these devices operate in the visible spectrum, the blood must be removed and replaced with saline to permit viewing. Since blood is opaque at visible wavelengths, angioscopy only works when the blood is pumped out of the artery and replaced with clear saline solution. As stated in *Arterial Imaging: Text and Atlas* (White, D. M., Chapman and Hall, 1993), "In order to obtain adequate visualization within the vessel lumen, blood must be removed from the field of vision as even small amounts of red cells can obscure the clarity of the image." In angioscopy, the catheter is directed to the arterial segment of interest and two occluding balloons are pressurized allowing the intervening blood to be removed and replaced with saline. An angioscopic catheter requires multiple ports: fluid pressure ports, an irrigation port and a port for the endoscope. Consequently, the devices are difficult to operate, since the physician must position the catheter, activate distal and proximal balloons, extract the blood from a port between the balloon and replace with saline. This cumbersome procedure, developed in the 1980's, has been used infrequently since it was very time consuming and presents a danger to the patient. The bulkiness of the angioscopic catheter, the complicated procedure and the inherent risk to the patient in having an artery totally occluded for the time of the procedure has made this procedure unpopular and relegated it to a few research-oriented hospitals. The disappointment with this technology has led to the development of a catheter ultrasonic technique called intraluminal ultrasound.

In an effort to produce visualization at the site of angioplasty for the surgeons, intraluminal ultrasound (for example, U.S. Pat. No. 4,917,097) devices have been designed. The intraluminal device is a modification of the familiar external ultrasound device used to visualize prenatal infants and heart valves. External ultrasound devices only have resolutions in the centimeter region. Greater resolution requires a higher greater frequency. The physics of the instrument dictate that the higher the frequency of the ultrasound transducer, the greater the potential for higher resolution and concomitant shorter penetration through the tissue. Higher frequencies do not penetrate as far requiring the transducers to be very near the structure. To visualize angioplasty procedures the resolution needs to be about 0.2 mm, requiring a 20 MHz device. A 20 MHz device will only penetrate about 1 cm of tissue before it is drowned in background noise. Consequently, for application in the coronary vasculature most of the device must be miniaturized so it can be inserted in the artery close to the blockage area. At a frequency of 20 MHz, it is possible to view the structures of the coronary artery only within a centimeter distance, requiring the transducers to be inserted in the artery. In one embodiment (U.S. Pat. No. 4,917,097) of this technology, a multitude of ultrasonic transducer crystals (64) are placed on the end an around the circumference of a 1.2 mm catheter to produce a visual view of the site of angioplasty. The catheter's construction is bulky because both the transducers and three integrated circuit signal processing chips have to be placed on the catheter tip. It is necessary to process the small signal with as little transmission through conductive wires. The positions of the electrical driver components (being external rather than internal) will generate ambient electronic noise, which contributes to the limitation of resolution from the catheter. The resultant picture is of marginal resolution quality because of the limited number or density of transducers, which corresponds to a 64-pixel image. The geometry of the catheter allows each pixel approximately 6 degree field-of-view of the wall of an artery. If the artery inner diameter were 5 mm, then each pixel would view 0.26 mm of the wall. This assumes there is not overlap of coverage by each pixel and there is no ambient noise in receiving the signal. Unlike light, which reflects off of surfaces, ultrasound is also absorbed to a significant degree by body tissue and then reflected; resulting in fuzzy or overlapping tissue interfaces in the image. Also, since the received ultrasonic signal produces only microvolts of response. At these frequencies, it is just above ambient noise. It is difficult to process a clear signal of this size when the system noise is very close to this amplitude. Thus the poor quality of the ultrasonic image is due to (1) small number of ultrasound transducers (2) absorption by internal tissue and (3) low signal to noise ratio. The arrangement of the receiving pixels and the transmitter produces a blind spot in the first 0.2–0.3 mm of the image. This blind spot causes difficulty in the visual interpretation of the image produced by this device Another embodiment that is used to view the coronary arteries is the IVUS catheter. It consists of a single spinning piezoelectric transducer, which operates on a sector scanning principle to produce its forward views. A stylet connected to the transducer is spun to provide images over a full circle. Side by side comparisons show similar results for this system and the one discussed above. Either approach is a poor substitute for optical pictures. With optical systems, a pixel could correspond to a single fiber optic bundle of which there are thousands in conventional endoscopes. Tissue surface definition is well-defined, since light scatters off of surfaces instead of being absorption by the tissue. Consequently, optical and ultrasound images are not comparable.

With the interest in electrical mapping and catheter ablation, cardiologists specializing in these procedures, called electrophysiologists, have searched for visualization techniques to assist them in these procedures. In these procedures, catheters are inserted to precise positions within the heart. Any visualization of these procedures would be extremely valuable. Researchers have focused on intracavitary ultrasound, a technology similar to intra-luminal ultrasound, but at lower wavelengths to see greater distances. Bom (U.S. Pat. No. 3,938,502), describes a crude ultrasound device for use in the heart and blood vessels. Like its vascular counterpart, this technology suffers from the inherent problems of ultrasound; poor resolution and insufficient differentiation of tissue surfaces. Obviously, there is no heart analog for angioscopy, since it is not feasible to replace blood inside the heart with transparent saline solution.

There is no known prior art on an infrared endoscope illuminating a structure through blood with infrared light and observing the returning reflected light from the structure. In medicine, infrared imaging is used in a very different manner; detecting cancerous cells which have different temperature, by measuring the emitted infrared radiation from the cell.

Infrared technology is principally used in medicine, in a different manner from the present invention; to identify abnormal or cancerous cells by measuring emitted radiation from body structures; a field called thermography. All warm or ambient objects radiate energy in the infrared, peaking at 10 microns, with measurable radiation seen as low as 2 microns. Abnormal cells radiate slightly differently and are therefore seen as objects of distinct color. The most common usage is mammography. When breast tissue is photographed with an infrared camera, cancerous tissue shows up as a different color indicating tissue of different temperature at that point. This principle has been applied to other parts of the anatomy, such as skin cancer. Additionally, endoscopes are disclosed in the art to measure similar cancer characteristics in internal body cavities.

With one exception discussed below, infrared endoscope art is limited to imaging the emitted infrared spectrum internal body cavities; no art has been found on internally illuminating the body cavity with infrared light. The endoscope needs to view the internal body cavity through air, since water is not transparent to emitted infrared radiation for most wavelengths. Adachi (U.S. Pat. No. 5,445,157) describes a thermographic endoscope sensing emitted infrared radiation from 9–11 microns, for the purpose of imaging temperature differences in abnormal cells such as cancerous cells in a gaseous medium. The image, corresponding to small temperature differences, is enhanced by means of injecting low-temperature gas out of the distal end of the endoscope. This device could not be used in a fluid medium such as blood because of the extremely high absorption values of blood at these wavelengths as discussed in the "Absorption of Water" section below.

Bonnell (U.S. Pat. No. 5,711,755) describes a means of imaging infrared radiation emitted from interior structures with an endpscope in the 2–14 micron region and combining it with a visual spectrum image for detection of abnormal cells such as gallstones. A preferred embodiment involves the use of a cooling fluid to further enhance the temperature discrimination sensitivity. This device would only "see" abnormal cells; ones that radiate at a slightly different temperature from the surrounding tissue. Normal cells radiate at the same temperature and would be filtered out through electronic processing and therefore could not be imaged. This patent teaches that using the visual spectrum image overlaid with the infrared spectrum image creates a composite image where cells of abnormal temperature appear as objects of different contrast on the visual image. This patent is concerned with detecting only emitted radiation, as there is no illuminating infrared light source. No mention is made of detecting this emitted radiation anywhere in the cardiovascular system (i.e. blood media). In fact, detection in a blood media would smear out temperature differences since the emitted radiation is so small. An infrared picture of the emitted radiation of a structure, through blood would not contain any image—even if abnormal cells existed.

Viewing a normal structure in a fluid media requires illumination at a higher power level than the normal emitted background, to produce sufficient reflectance for optical imaging. The emitted radiation detected in U.S. Pat. Nos. 5,445,157 and 5,711,755 are background radiation which obscures the image and requires light sources with higher wattage to "flood" the field. There is no art found using illumination at infrared wavelengths through a fiber optic bundle to produce images of an internal body structure using the reflected and scattered illumination collected by an endoscope.

Nakamura (U.S. Pat. No. 4,953,539) describes an endoscopic imaging device placed in an organic body and illuminated external to the body with infrared radiation in an effort to visualize the reverse surface of internal organs such as the bladder. Nakamura teaches that if an organ is backlit externally with infrared light, the reverse surface can be visualized with an endoscope inserted internal to the organ and sensitive to at least infrared light. Infrared light is chosen as the illuminating source since tissue has lower permissivity in the infrared region; it penetrates further through tissue. With this arrangement, the reverse surface of the tissue is said to be visualized. There is no teaching, references, or prior art citations referring to visualizing structures through opaque fluids such as blood. The Nakamura teaching is illuminating the organ externally with infrared light, and is not relevant to internally illuminating with infrared light at particular wavelengths which render liquid with suspended particles such as blood semi-transparent.

Unrelated to thermography and infrared imaging, Boutacoff (U.S. Pat. No. 5,147,354) describes a mid-infrared endoscope that is used to deliver or transmit infrared energy for laser surgeries. He discloses an endoscope operating between 1.8–2.2 microns which corresponds to commonly used lasers which have wavelengths in that region for the purpose of ablating and welding internal structures such as within the human knee. There is no suggestion of imaging structures in the infrared region. The wavelength spectrum was chosen at a water absorption peak (where water is more opaque), creating more localized heat which is used in welding and ablating tissue. This would be entirely unsuitable if applied to the present invention. Boutacoff refers to an endoscope suitable for transmission of infrared energy of commonly used lasers; no mention is made of imaging structures with infrared energy.

The prior art presented on infrared endoscopes does not disclose or suggest using internal infrared illumination through a fiberoptic cable, to illuminate structures in an opaque-body-fluid environment, such as blood, and viewing the scattered light from the structure to form an image.

SUMMARY OF THE INVENTION

For imaging through blood, after considering absorption by hemoglobin and water, and the scattering by red blood cells, wavelengths are identified to permit longer viewing distances in excess of five millimeters. The emitted radiation of the structure itself, which dominates the patent literature on infrared endoscopes, is of no interest to the present invention; except that it would in some cases be viewed as noise. For example, in the case of an infrared endoscope operating at a wavelength of 4 microns, there is a measurable amount of emitted radiation at that wavelength. Consequently, the internal light illumination light intensity would need to be greater than the intensity of the emitted radiation; the field of view would need to be flooded with internal illumination to overcome the emitted radiation.

It will be seen that "viewing distance" through blood is determined from the absorption of hemoglobin, the absorption of water and the scattering by the red blood cells. Accordingly, each of these factors will be considered individually. Absorption and scattering are fundamentally different: absorption can be overcome with sufficient power, while scattering is mostly unaffected by power level of the light source. Absorption of hemoglobin and water are considered first, followed by a detailed discussion of scattering.

The present invention describes a flexible, semi-flexible or rigid endoscope which can "see through" opaque body fluids, such as blood. Fluids become opaque from the presence of mostly suspended cells as well as other particles. Conventional endoscopes which use visual spectrum light (light with wavelength between 0.3–0.75 microns), are unable to visualize through opaque fluids, such as blood. It has been discovered (and disclosed below) that certain wavelengths in the infrared region (0.8–11 microns) permit the light to "see around" the suspended cells while not being extinguished by water (which is highly absorptive in this region). The method and apparatus disclosed below are applicable to any opaque body fluid; however, from a medical point of view, the most important one is blood. Consequently, blood is considered throughout this teaching as an example of a liquid with suspended particles. Blood is opaque in the visible spectrum because of the suspended cells—the red blood cells.

This patent application provides a method and apparatus embodiments to visualize structures through opaque body fluids, such as blood, using infrared wavelength illumination. Body fluids are opaque because of suspended cells in the water medium. Cells typically have dimensions in the 1–20 micron region. A fundamental teaching in this patent is that these dimensions prevent view visible light since the scattering by the suspended particles is far too high. If these suspensions are illuminated with infrared light comparable to cell dimensions, the scattering decreases inversely as the square of the wavelength. Since blood is the principle opaque body fluid, it is used throughout as the representative example. Blood primarily consists of water and disk-shaped red blood cells containing a concentrated hemoglobin solution and occupying about 35% of the blood volume. The red blood cells have an average diameter of 7.7 microns and a width varying from cell center to edge of 1.4–2.5 microns. Viewing distance is limited by scattering of the red blood cells and absorption by water and hemoglobin. As disclosed below, there exist wavelength regions where these factors are low enough to permit viewing of structures in the centimeter-region through blood.

This is accomplished by providing internal infrared illumination thought an endoscope placed near the structure, and collecting the reflected and scattered light from the structure. Conventional endoscopes (which use visible wavelengths) do not penetrate these environments because of light scattering by the suspended particles. A principle teaching is that scattering in opaque-body-fluid environments, such as blood, is improved dramatically by using wavelengths in the infrared, which are comparable to particle dimensions. However, the major component of body fluids—water—becomes mostly opaque in the infrared spectrum. A second principle teaching is that only certain infrared wavelength regions are semi-transparent to water and hemoglobin. Combining these principles, the wavelengths satisfying the dual criteria of low scattering by the suspended cells and low absorption by water and hemoglobin are the wavelength regions: 1.4–1.8, 2.1–2.4, 3.7–4.3, 4.6–5.4 and 7–14 microns. In these regions, structures can be visualized at various distances, depending on light source power and wavelength, through a liquid with suspended particles, such as blood.

The higher wavelength regions, 3.7–4.3, 4.6–5.4 and 7–14 microns require higher intensity light sources because water absorption is much higher in these regions. Accordingly, light sources in these regions can employ a pulse configuration light source. In this configuration, a high-intensity light source is applied for very brief periods in synchrony with the cardiac cycle. These light sources will permit very clear images of structures through blood at a maximum distance limited by the absorption properties of water.

In addition, to the imaging properties of these instruments, they can be altered to provide spectrometric data of the objects within the field-of-view. The light sources used for illumination can be either continuous or discreet depending on the application. The nature of the spectrometric data can be non-imaging or it can be processed to become imaging spectrometry. To produce the spectral separation either end of the endoscope can be modified with the optical elements to produce the spectral components.

Depending on the size of the endoscope, the region that is being observed, an endoscope in its flexible, semi-ridge, or rigid form can be modified to accommodate surgical tools and diagnostic probes. These tools and probes can be used and observed during their insertion while they are in the field-of-view of the endoscope.

When the endoscope is used inside the heart, or a region that is affected by the motion of the heart, the imaging processing module can be used to provide image compensated for motion, or freeze frame viewing, that is specifically timed to periods of the heart's cycle. An example of this use can be contemplated in the valve region. The valve leaflets have motion associated with their opening and closing, and the magnitude could be as much as 12 mm or more. If the endoscope were located close to the moving portion of the leaflets, then viewing would result in a smeared almost unrecognizable object. The image processing can provide a timed delayed or slow motion option for viewing, or a stop action shot at the same time during the heart's cycle. This processing option will allow close examination of moving walls inside or outside the heart.

Conversely, when it is desired to view the motion of a structure, multiple images can be taken to image the motion. For example, myocardial infarctions are akinetic; they do not move during a cardiac impulse. If multiple images are acquired during heart contraction, the akinetic or infarct areas could be determined.

An endoscopic imaging system, transparent to blood, would have enormous consequences in observing malformations, assisting catheter navigation, diagnosing cardiac conditions and observing procedures inside the heart or in the vasculature. The scope of this invention is not limited to cardiology but extends to other fields as well such as neurology and oncology. In addition, having "sight" in the vasculature will lead to many procedures unforeseen at this time. Today, laparoscopic procedures include suturing, excising and stapling. Similar procedures could be adapted for the cardiovascular system if the procedure could be viewed.

Malformations in the heart include congenital malformations and progressive deterioration of structures such as valves. Common congenital malformations are transposition of the heart or arteries, septal defects and valvular insufficiency. In transposition of the heart or arteries, the surgeon has no diagnostic means of assessing the exact nature of the transposition prior to surgery. A blood-transparent endoscope would enable a thorough examination of the nature of the transposition permitting proper preparation before surgery. Septal defects are holes in the walls of the heart, which are also repaired in open-heart surgical procedures. If the exact location of the septal defect could be visualized, minimally invasive catheter procedures have been developed to place a plug in the defect (hole) and the pediatric patient would avoid open-heart surgery. The most common malformations are valve defects, which prevent the full opening or closing of the valve called valvular insufficiency. Currently valvular insufficiency is diagnosed by external ultrasound (echograms). This technology is far to crude to specify the precise nature of the insufficiency—only its occurrence.

Valvular disease has different origins. One important distinction is deciding if the disease is vegetative in nature or a structural defect. If the valve could be visualized by an endoscope, this distinction would be very apparent. Also, small structural defects are repairable by a catheter with an expandable balloon; a procedure called valvuloplasty. Currently, this procedure uses only radiography for feedback and as result has had marginal success. Obviously, visualizing the valve leaflets and the catheter would be of great benefit in making this procedure practical. As mentioned above, laparoscopic type procedures such as suturing or stapling could be used to repair the valve without the need for open-heart surgery.

Valves also can be natural or artificial. Observing the artificial valve, in vivo, has never been possible; consequently, artificial valve failure is often catastrophic. If the artificial valve surface could be visualized, cracks and other structural failures could be diagnosed before valve failure. Valves are also attacked by blot clot formation. Patients take a blood thinning substance called COUMADIN (Registered Trademark) or generic alternative to prevent clot formation on valve surfaces. A blood endoscope would observe clots in their early stages allowing modification of the dosage or drug. Moreover, minimal surgical procedures would be possible if there was an image of the procedure.

An important use of an infrared endoscope, in the heart, is to provide a visual guide for cardiac catheters navigating the vasculature. Catheters are inserted in the leg, arm or neck and snaked through the appropriate vasculature branches to the cardiac chamber of interest. Catheters are routinely placed in specific areas of the left and right atriums, left and right ventricles and the coronary sinus. Navigating the vasculature, to arrive at these destinations can be a troublesome procedure. This is currently accomplished by viewing the fluoroscopic image of the patient's chest. This image provides the physician with a faint image of the heart and its relation to the catheter, which is much brighter since it, is metallic or has fluoroscopic markers. If the catheter is positioned in the wrong branch of the vasculature, it eventually becomes apparent from the fluoroscopic image. At that point the physician retracts the catheter, rotates and tries again. He might even fully retract the catheter, reshape it and insert it again, hoping the new confirmation will allow catheter passage through the appropriate branches in the vasculature. Small branches of coronary arteries usually require many attempts before the correct branch is reached. Visual images of the catheter and the branch in the vasculature would make this procedure much considerably easier and quicker. This embodiment could be accomplished by incorporating a visual guide with its own retractable guide wire. When a choice in direction is needed, the guide would extend and force the catheter to follow in a specific direction. If an image of the catheter reaching a branch in the vasculature were available, the physician could maneuver the catheter into the correct branch. Additionally, visualization will allow passage of smaller arteries previously not considered navigable, permitting angioplasty procedures and other therapies in these small arteries.

Using current techniques, once the appropriate chamber is reached, locating a specific area of the chamber can prove to be equally difficult. Pacing and defibrillator electrodes are usually placed in the right atrial wall or appendage and the apex of the right ventricle. Frequently, chordae, tendons in the heart, and the vigorous motion of the heart can prevent easy insertion in these areas. In electrophysiologic studies, many catheters are inserted in precise places in the heart, usually near cardiac valves, the coronary sinus and the right ventricle. Each catheter has four equally spaced ring electrodes. Since 'touch and feel" is used to guide the catheter, it cannot be precisely located in the region of interest and it is hoped that one of the four electrodes is lying over the region of interest. Assessment of catheter positioning is deduced from the electrographic recording on each electrode. This is a time consuming procedure of making small adjustments in the catheter position, assessing the electric potentials and if not situated correctly repeating the entire procedure. In all these cases, a blood endoscope would show the relation of the catheter to internal cardiac anatomy greatly facilitating catheter positioning.

Some procedures not only direct the catheter to a region of interest in a cardiac chamber, but also modify the endocardial surface. Most arrhythmias occur due to a short circuit in the electrical conduction somewhere within a cardiac chamber. Catheter ablation is a procedure where the catheter burns a small hole in the endocardium to eliminate the arrhythmia. This is a very time-consuming process to precisely find this small arrhythmic zone, usually requiring precision on the order of a millimeter. Usually, these zones occur on the borders of the different types of tissue; often around the annulus of cardiac valves. A mid-infrared endoscope would make this procedure more precise and of shorter duration if this area could be visualized through blood. Since guidance is currently done blindly, only the cases where the arrhythmogenic zone is well defined and localized is catheter ablation attempted.

With the assistance of an infrared endoscope many more complicated procedures could be attempted. Potentially, the two most important arrhytmias in terms of morbidity and mortality are atrial fibrillation and post myocardial infarction ventricular tachycardia. Atrial fibrillation can be eradicated by cutting the atrium into sections (MAZE procedure). This surgical procedure has been attempted in catheter ablation; the strategy is to connect many burns to form a set of linear lines in the atrium. Currently this procedure is very lengthy and not successful enough to merit widespread usage. A mid-infrared endoscope could visualize the burns and make this a standard procedure. Post myocardial infarction induced ventricular tachycardia, like the MAZE procedure has an open-heart surgery counterpart. There is a procedure called a ventricularotomy in which the surgeon makes incisions around the myocardial infarction thereby disrupting the arrythmogenic zone and hence the tachycardia. Post-myocardial-infarction ventricular tachycardia is the most lethal and difficult to treat of tachycardias. Today the standard treatment is defibrillator implantation. It arises because the myocardial infarction has incomplete borders which can short-circuit intrinsic conduction. A catheter ablation strategy suggested for the treatment of this arrhythmia is to burn a series of connecting dots or lines around the circumference of the infarction to eliminate the short-circuit. A infrared endoscope could visualize the myocardial infarction since this tissue is akinetic and burn lines of connected dots placed around the infarction.

Besides cardiology, several other medical disciplines would benefit from an infrared endoscope. In neurology, strokes are the major cause of mortality. Recently, new techniques allow new methodologies to treat strokes acutely within hours after onset. Techniques include, for occlusions: angioplasty, local infusion of streptokinase and TPA. For burst arteries, there exist metallic coils which can be inserted to plug the hole. Observing visually the procedure would simplify this procedure as well as verify the outcome.

In oncology, a current strategy is to manage the blood supply leading to the tumor. Drugs called angio-inhibitors are now available which inhibit blood vessel formation. Infusion of these drugs has shrunk tumor size by interfering with the blood vessel supply feeding these tumors. The efficacy is determined periodically from magnetic resonance image scanning of the tumor. A much more sensitive method would be to measure the size and characteristics of a vessel feeding the tumor by inserting the blood endoscope.

In summary, imaging cardiovascular structures would be immensely valuable in diagnosing cardiac malfunction, in guiding most interventional cardiology procedures and would permit the development of new therapies not only in the heart but anywhere in the vasculature. This invention discloses an endoscope (and associated components) operating at infrared wavelengths. Infrared wavelengths are chosen because they are longer than the particles in blood (red blood cells). The use of infrared systems for the purpose of seeing through particulates is well known but almost always in an air medium. It will be seen that the same principles used in infrared weather satellites and in infrared telescopes apply to blood.

BRIEF DESCRIPTION OF DRAWINGS

FIG. 10 is an illustration of the usefull bands in the electromagnetic spectrum, which can be used to see through suspended particles in water. Expected viewing distances for blood based on scattering is indicated for each region.

DETAILED DESCRIPTION OF THE INVENTION

The present invention draws upon several different scientific phenomena and medical technologies to achieve a method and device useful for imaging through blood and other liquids with suspended particles. To properly understand the pioneering scope of the present inventions, the relevant technologies are first briefly discussed, and several embodiments of the invention are then described.

INFRARED ENDOSCOPES

Figure 1:
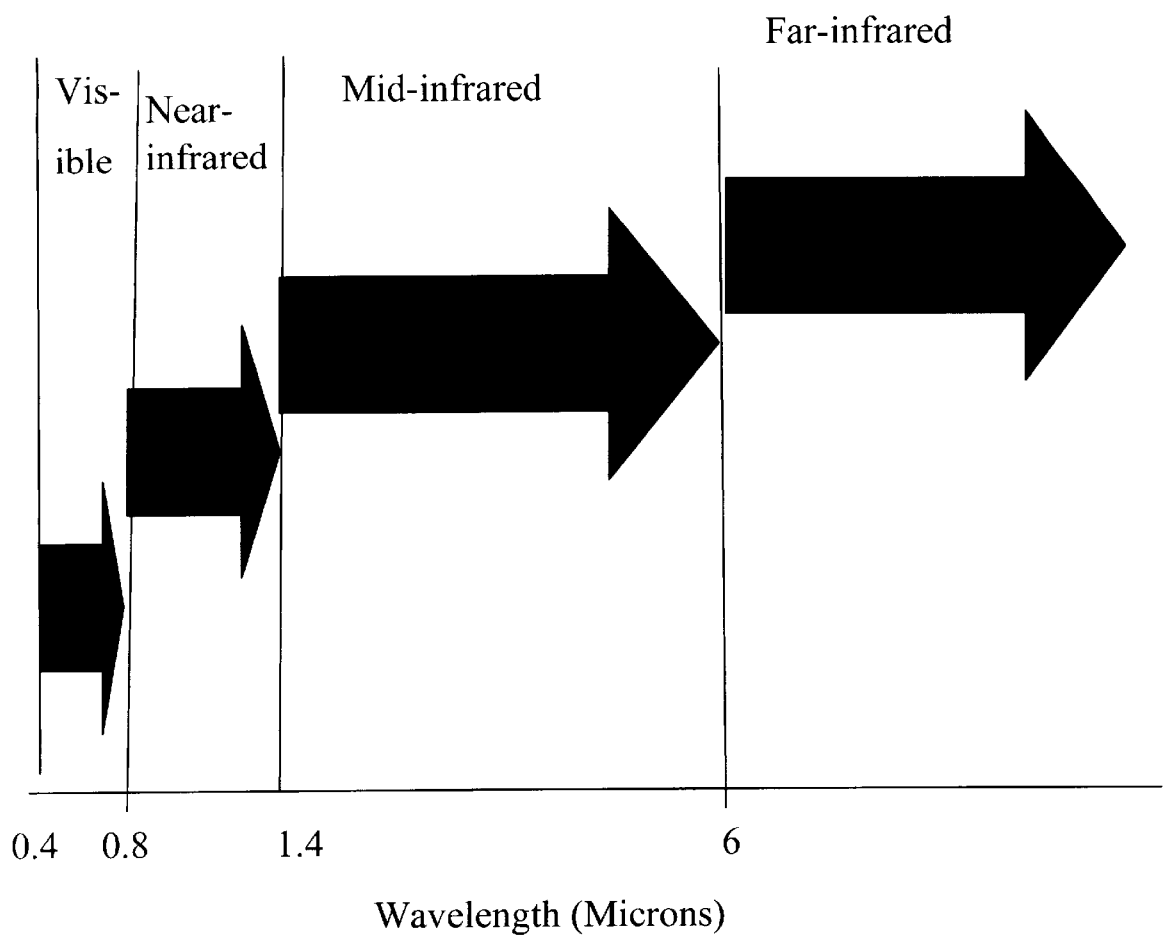
FIG. 1 is a graph of the electromagnetic spectra, showing the wavelength region used herein.

The electromagnetic spectrum (FIG. 1) extends from microwaves to gamma rays as wavelength decreases. In the middle is the visible spectrum used in normal vision, and the spectrum used in endoscopes today, spans a range of approximately 0.3–0.7 micron wavelengths. The infrared spectrum is traditionally divided into three spectrums: near, mid and far-infrared. The dividing points of the spectrum are somewhat arbitrary, depending on the application. In this patent, they are defined as follows: near-infrared extends from 0.8–1.4. microns, the mid-infrared region extends from 1.5–6.0 microns and far-infrared spans 6.0–15 microns. The mid-infrared and far-infrared wavelength region encompass the applications which the disclosed flexible, semi-flexible or rigid endoscope is preferably manufactured.

Within the mid-infrared region, there exist four sub-regions: 1.5–1.9, 2.0–2.4, 3.7–4.3 and 4.6–5.4 microns where scattering and absorption characteristics are especially favorable for viewing structures through blood. Additionally in the far-infrared, the region 7–11 microns is also favorable, especially from a scattering perspective. Some of the optical components need to be altered to maintain highest optical efficiency. Camera sensors, the size and flexibility of the fiber-optic element and the chemistry and power of the laser diode or laser all change with wavelength. With increasing wavelength, the power of the light source significantly increases, the fiber-optic becomes larger and less flexible, while the cameras become more complex. Depending on the distance, flexibility requirement and cost, an appropriate wavelength region can be defined for an endoscope viewing structures through blood in the cardiovascular system.

ABSORPTION
A. ABSORPTION BY HEMOGLOBIN

Light does not penetrate through blood at visible wavelengths, because of absorption by hemoglobin and water and scattering by the red blood cells. Blood consists mostly of plasma and red blood cells. Plasma is a semi-transparent, straw-colored liquid composed of 91% water; the remainder being protein (7%), lipids (1%), inorganic metals (1%) and miscellaneous extractives. Thus, the dominant component of plasma is water. Blood cells are concave-disc shaped bags of concentrated hemoglobin solution. Red blood cells constitute about 35% of blood volume. From an absorption point of view, transmission through blood is equivalent to viewing through concentrated hemoglobin bags in an aqueous solution.

Absorption is an optical property of any material or liquid that relates the amount of energy to loss in transmission per unit length. Scattering is another optical property relating the light reflecting and diffracting from particulates or particles suspended in media such as red blood cells in plasma. These optical properties are both related to wavelength. Scattering is also related to the physical size of the particles and the ratio of the indices of refraction of the media and the particles. Both of these decrease the intensity of the received signal exponentially by a value:

$$\text{Transmission} = \exp[-(\alpha(\text{hemo}) + \sigma) \times l] \qquad \text{Equation 1}$$

Where l (cm) is the distance of the target structure through blood and $\alpha$ (hemo) and $\sigma$ are the extinction coefficients due to absorption and scattering respectively. Later, as infrared wavelengths are approached, this equation will include an additional term for the absorption of water; however, water is transparent in the visible region so this term is negligible.

Since Equation 1 is an exponential equation, the reduction of light can be severe. If the sum is 10 (1/cm), it is reduced to 0.0004%. Even this severe attenuation can be compensated for by using more powerful laser-diodes or lasers. Also, more sensitive light detectors in the camera decrease the amount light needed to register an image in the camera. When the total extinction coefficient is 40, light has been attenuated to 4×10(−18) of the incident light at a distance of one centimeter; however, at a one-millimeter distance, 2% of the initial light is still present.

If it is assumed that three millimeters is the minimum useful distance to visualize an average-sized coronary artery, estimates of light source power can be made as a function of peak absorption using Equation 1. Conventional infrared cameras in this application can register an image if the received back-scattered light is about 0.01–0.1 milliwatts. If the total extinction coefficients in Equation 1 equal 30, a light source pulse of about 400 watts would be required. If the coefficients equal 20, a light source pulse of about 20 watts would be required. If they only equal 10, a light source only about 1 watt would be needed. When one considers the absorption of hemoglobin, only regions where the absorption extinction coefficient is less than about 30 are deemed of primary interest. Higher absorption extinction coefficients require more exotic high-energy light sources.

Figure 2:
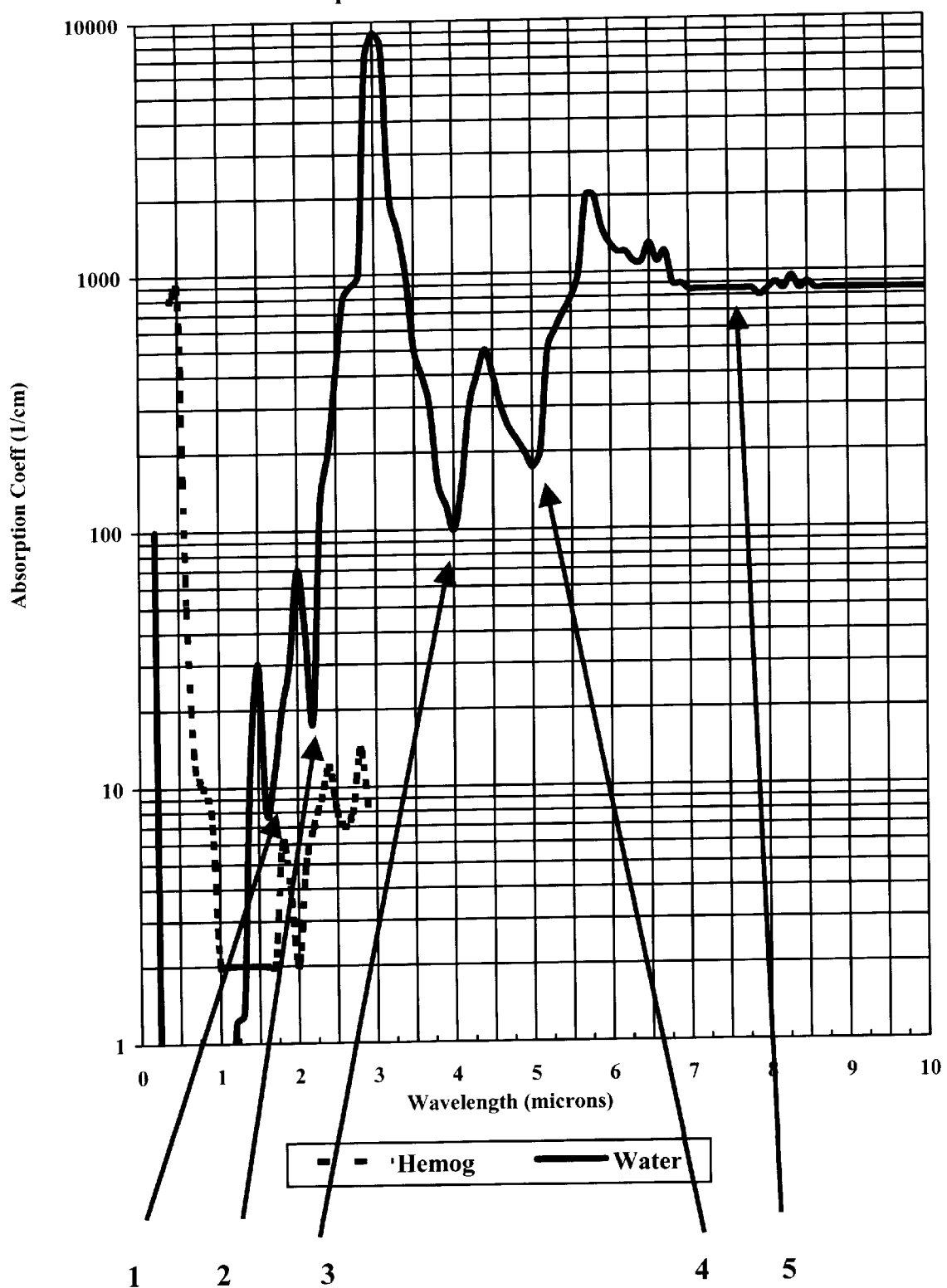
FIG. 2 is a graph of hemoglobin and water absorption versus wavelength extending from the ultraviolet to the far infrared.

When the absorption spectrum of hemoglobin is considered versus wavelength, several interesting features are apparent (FIG. 2). Hemoglobin is most absorptive in the visual spectrum reaching a peak absorption of 10,000 (1/cm)—far too large too see anything. This partially explains the difficulty of seeing through blood with visible wavelengths. It is not until the wavelength lengthens to the near-infrared where the absorption descends to a value of around 10 (1/cm) that viewing distances in blood is feasible. As seen in FIG. 2, the absorption of hemoglobin reaches a minimum of 10 (1/cm) at 0.8 microns, followed by an increase to about 20 (1/cm) at 1.0 micron wavelength and then returns to a value of 10 (1/cm) throughout the infrared spectrum.

From a hemoglobin absorption perspective, viewing structures through blood is only feasible for wavelengths exceeding 0.8 microns. Experimentally, a noticeable improvement is observed in viewing structures through blood at a wavelength of 0.88 micron. At this wavelength, viewing structures through blood, distances of about 1 mm could be achieved. It will be shown below, that scattering prevents longer distances—this is the $\sigma$ term in Equation 1.

ABSORPTION

B. ABSORPTION BY WATER

The attraction of using illumination with wavelengths in the infrared region to "see through" blood is counterbalanced by the increased opacity of water as wavelength increases. Water is only transparent in the visible and near-infrared regions. As the wavelength moves to the infrared, the absorption of water increases in band formations with many local maxima and minima (FIG. 2). In FIG. 2 the local minima are labeled 1–5. These bands are due to resonance phenomenon by water molecules as they stretch or rotate at particular wavelengths. Since plasma is composed of 91% water the location of the minima and maxima are expected to occur at the same points as for water. Moreover, the entire shape of the curve is expected to be similar to the curve for water. The actual values of the extinction absorption coefficient, however, will be smaller than in free water. Since the high absorption in water are due to a resonant motion of the water molecules, any debris disturbing this motion will effectively lower the absorption extinction coefficient at the wavelength corresponding to that resonance.

At a wavelength of about 1.5 microns, the absorption of water—called $\alpha$ (water) is comparable to the absorption of hemoglobin—$\alpha$ (hemo)=$\alpha$ (water). Thus, in the infrared region, Equation 1 needs to include the absorption term for water in proportion to its presence. Since red blood cells constitute 35% of blood, and about 65% water, this equation is waited for these two principle components, the infrared transmission for blood becomes:

Infrared Transmission=exp[−[0.35$\alpha$(hemo)+0.65$\alpha$ (water)+$\sigma$]×l]   Equation 2

Equation 2 is the general equation describing the decrease in intensity in blood at a distance 1.

The absorption in FIG. 2, indicate that these values are achieved only for a few wavelengths between 0.88–2.3; those wavelengths near the local minimums of 1.6 and 2.1 micron, denoted in FIG. 2 as 1 and 2 respectively. It is noted that water absorption local maxima occur at 1.6 and 1.9 microns. At their peaks, water becomes much more absorptive. Consider the region between 1.6 and 2.2 microns (Table 1). At local maxima (1.4, 1.9), light is absorbed by water so that a large powered laser would be needed to see through even 0.5 cm. However, to view a 0.5 centimeter distance, light at 1.6 and 2.1 micron wavelengths require dramatically less energy: about 10 milliwatts for the 1.6 micron source and about 1.5 watts for the 2.2 micron source.

TABLE 1

| Wavelength (microns) | Water Absorption (1/cm) | Est Watts for 0.5 cm |
|---|---|---|
| 1.4 | 50 | 1.3 × E + 11 |
| 1.6 | 8 | .01 |
| 1.9 | 200 | 3 × E 43 |
| 2.1 | 18 | 1.48 |

FIG. 2 shows a peak absorption value at 1.9 microns. This peak has an absorption extinction coefficient of about 200 (1/cm)—preventing viewing at even sub-millimeter distances. Beyond 2.3 microns, the other possible wavelength is 4 and 5 microns and perhaps 7–11 microns depending on the absorption extinction coefficient for plasma at that wavelength.

In the mid-infrared region (1.5–6 microns), water absorption curve reveals four regions where the local water and hemoglobin absorption are at a minimum: 1.5–1.8 microns, 2.1–2.4 microns, 3.7–4.3 microns and 4.6–5.4 microns. In FIG. 2, these are labeled as 2, 3 and 4 respectively. For example, in the case of the 2.1-micron wavelength, intensities of about a watt or less would illuminate a structure displaced one-centimeter in blood. These regions will have the lowest overall absorption extinction coefficient. In the mid-infrared region, absorption in water and hemoglobin can be significantly reduced by employing wavelengths centered at 1.6, 2.2, 4.0 and 5.0 microns and providing illumination intensities great enough to counteract the absorption of water.

Examining the next region from 3.8–4.2 microns, water appears to have a minimum absorption of about 200 (1/cm) while hemoglobin only has an absorption of 8 (1/cm). Placing these values in Equation 2 yields an average coefficient of 87.3 (1/cm)—preventing viewing distances through blood beyond a few millimeters. However, the actual absorption extinction coefficient for blood has not been measured in the literature. While the shape of the curve is expected to be similar to water, the magnitude of the absorption extinction coefficient for plasma is unknown—but certainly smaller. As free water is contaminated with other entities, the overall absorption extinction component decreases since the water molecule is not as free to rotate and stretch. Experiments with low-powered infrared lasers suggest it may be substantially lower than reported in the literature for water.

The exact physical relationship from the mix of plasma and red blood cells and its affect on infrared transmission through this media is not completely understood or found in publications. Each of the peaks and valleys in the water absorption curve shown in FIG. 2 corresponds to motion of the water molecules, such as stretching, bending and rotating. Most solutions are not opaque in the infrared because these motions are eliminated or severely reduced. The concentrated solution inside red blood cells is a good example. Although concentrated hemoglobin solution is about 35% hemoglobin and 65% water, it is semi-transparent in the infrared region, with an extinction coefficient of about 8 (1/cm). Plasma, unlike pure water has many substances (9% of plasma volume) dissolved and floating around besides red blood cells. Their presence will result in substantially lower absorption values than the values for water in FIG. 2.

In addition, precise wavelengths in the 3.8–4.2 microns region are likely to have smaller absorption than neighboring wavelengths since each minima and maxima has considerable sub-structure. FIG. 2, as well as other references on the absorption of water, have been tabulated for the meterologic field. Accordingly, choice of the wavelength increment is chosen arbitrarily among investigators. The wavelength increment can strongly affect both the minima and maxima absorption. A finer wavelength increment, examining just this wavelength region, will reveal the substructure, which might include wavelengths where absorption are substantially lower than those listed in FIG. 2. Also, most data has not used a monochromatic light source such as a laser or laser diode. The use of multi-wavelength light sources will tend to smear out sharp rises or declines in the absorption as a function of wavelength. If there is a sharply defined wavelength with a much smaller absorption, it would not be observable in measurements such as FIG. 2.

Another factor, which will result in lower absorption for blood, is the number of red blood cells contacting each other and therefore providing a low absorptive pathway over the path-length of the cell agglomeration. Cell agglomeration or Rouleax formation refers to the surface tension of groups of cells into lines of 5–10 cells. Each of these provides a low absorption pathway of up to a 80 microns. Multiple groups of connected red blood cells will provide a low absorptive pathway where only small distances need to be traversed through water—thus, lowering the effective absorption extinction coefficient Even if the actual absorption is still high—it can be compensated for by greater intensity light sources for blood without causing tissue or blood damage. High absorption can be compensated for by using large laser diode intensities in a pulse configuration. Since the endoscope can take a picture in 1–5 microseconds during a heart beat, the infrared endoscope can be employed with a very low duty-cycle of about 1:1,000,000, permitting blood and tissue to cool to their original temperature between cycles. At this pulse width, it is calculated that thermal transmission would occur over only a few microns—less than a cell diameter. The illumination pulses provided by the laser diode are so short in duration that the surrounding media does have sufficient time to convert the energy into heat. In fact, with this duty cycle, short pulses of thousands of watts can be employed without tissue or blood damage.

A further benefit of the 4.0 wavelength region is its inherent low scattering—permitting high resolution images to be photographed. One application of this system would be the microscopic examination of stents or artificial heart valves. In heart valves, small fissures occur prior to catastrophic failure. The 4.0 micron system would provide high resolution images of the valve surface in-vivo. Whatever minimum absorption is found for blood in this wavelength region, this wavelength would be useful in detailed examinations of structures up to whatever distance is permitted by the actual absorption value, the intensity of the light source and the sensitivity of the infrared camera.

The next region in the mid-infrared where water has a local absorption minimum in the region 4.6–5.4 microns. This region has an absorption extinction coefficient in free water of about 400 (1/cm). As in the 4.0-micron region, the actual minimum absorption value is unknown for blood. Scattering is further improved at this wavelength, malign this wavelength even superior than the 4.0-micron region for detailed examination of structures.

The last region in the mid-infrared is the broad region 7–11 microns. In FIG. 2, this broad minima is labeled as 5. The absorption extinction coefficient is about 700 (1/cm) for free water—far too high to see meaningful distances. In blood, however, there is. experimental evidence with CO2 lasers operating at a wavelength of 10 microns in a blood field indicating substantially smaller absorption than those measured for free water. A more finely granulated wavelength increment will reveal the lowest overall absorption extinction coefficient for this region. Scattering is at a minimum in this wavelength region, permitting the clearest viewing at whatever distance is permitted by the actual minimum absorption extinction coefficient for blood.

In summary, the regions centered at 1.6 and 2.1 microns have the lowest absorption in the mid-infrared region (1.5–6.0 microns). The absorption extinction coefficients for blood and water combined, applying Equation 2, are only about 8 (1/cm) for a 1.6 micron wavelength, and about 14 (1/cm) for the 2.1 micron wavelength. Centimeter illumination distances can be achieved with light intensities about or under one watt. As wavelength increases, the regions centered at 4, 5 and 9 microns will have higher absorption as wavelength increases. However, these regions will have substantially lower absorption than other wavelengths in that region. Depending on the actual measured absorption for blood, clearer images of cardiovascular structures will be permitted—up to a distance in blood where the light becomes extinguished.

This discussion has only considered the absorption part of Equation 2. In addition to increasing values of absorption, scattering also decreases signal intensity. Like absorption, the scattering coefficient changes with wavelength and unlike absorption it cannot be compensated for by increasing light source intensity. It will be shown that when scattering is included, the longest viewing distances through blood are achieved at wavelengths 1.6 and 2.2 microns. Even though the 0.88–1.4 micron region has small absorption for hemoglobin and water, high scattering from the red blood cells seriously degrade the image—allowing viewing distances through blood of only about 0.1 cm.

It is shown below that scattering decrease as the wavelength lengthens. Red blood cells are particles suspended in a media much like water droplets in air or metal particles in water. There are many examples (in dissimilar applications) of viewing greater distances through particulates by increasing the wavelength; infrared astronomy, infrared satellite photos and seeing through smoke and fog.

SCATTERING
A. CHARACTERISTICS OF PARTICULATE SCATTERING

Infrared imaging technology is employed when it is desired too see through particulates in the air, such as haze or fog, that are impenetrable in the visible spectrum. For example, near infrared cameras in satellites penetrate ground haze, while visible spectrum pictures remain hazy. Infrared telescopes see much farther than visible telescopes since they see through intergalactic dust. Much of our knowledge about infrared imaging has been developed from applications.

The basic principle behind these applications is—visibility improves once the wavelength of the light increases to a value comparable to the particle diameter. For example, ground haze consists of particles on average of about 1 micron in diameter. At a wavelength of 2.0 microns, visibility significantly improves because scatter has decreased with longer wavelengths compared to results in the visible region. It cannot see through fog, which consists of 10 micron particles. It is reported that using a 10-micron wavelength camera, a six-mile visibility could be achieved through dense London fog. Intergalactic dust consists of particles such as silica averaging about 1 micron in diameter. Infrared astronomy "sees through" these particles using wavelengths much in excess of 1 micron. The galaxy spirals were observed using infrared telescopes where visible spectrum telescopes had "blurred vision", losing the shape of the spirals.

This ability to "see through" particles at wavelengths exceeding particle diameter is a general characteristic of wave phenomena. Consider an example of stationary boats on a sea. One observes boats smaller than the crest spacing of the waves (wavelength), bobbing in the water with the wave front unaffected by the presence of the boat. The waves are reflected and scattered from the hull, so that transmission or the passage of the wave is blocked. Boats many times larger than the wavelength do not bob nearly as much; the wave front is strongly affected by the boat; it is scattered. The latter situation is analogous to viewing blood at visible wavelengths: the particles are, of course, many times larger than the wavelengths used by the optical systems.

Particulate interaction with illumination versus wavelength is an issue of scattering. From an imaging point of view, scattering is a much more serious problem since it results in loss of angular correlation. Absorption can be compensated for, to an extent, by increasing the wattage of the light source. Scattering is seen as first fuzziness and eventually cloudiness in the image. Understanding scattering characteristics is the key to improving images in the presence of suspended particles.

There are three regions types of scattering depending on the ratio of the particle radius (a) to the light wavelength $\lambda$. For $a/\lambda \ll 1$ Raleigh scattering prevails and the scattering is proportional the fourth power of $(1/\lambda)$. This is one explanation for blue skies and red sunsets. Red has a longer wavelength than blue; blue scatters more, red transmits better. The region when $a/\lambda \approx 1$ is the most difficult to analyze. The basic solution for particulates shaped as a sphere was developed by G. Mie in 1908—called Mie Scattering.

In this region, scattering is a complex function of $\lambda$, it oftentimes has a scattering proportional to the second power of $(1/\lambda)$. Once $a/\lambda \gg 1$, scattering is independent of $\lambda$.

| a/$\lambda$ | Name | Scattering Dependence on $\lambda$ |
|---|---|---|
| <<1 | Raleigh Scattering | $1/\lambda^4$ |
| ~1 | Mie Scattering | $1/\lambda^2$ or complicated function of $\lambda$ |
| <<1 | Reflective Scattering | independent of $\lambda$ |

A classic example of the last two regions is in viewing tobacco smoke passing through a beam of light perhaps entering from a window. Tobacco smoke consists of particles about the same diameter as the visible wavelengths (0.6 microns). When smoke passes through the light beam, the scattered light is mostly blue, since blue scatters more than red or yellow. After the smoker inhales the cigarette, the exhaled smoke now appears white since the particles are much larger than visible wavelengths, having been hydrated by the lungs. The white appearance of the exhaled smoke indicates the scattering is independent of the wavelength. This is the situation for viewing blood at visible wavelengths; the red blood cells are many times larger than the wavelength. This suggests extending wavelengths into the Mie region would be of great interest in the problem of seeing through blood.

B. MIE SCATTERING

Mie derived a solution for spherical metal particles in a fluid medium to explain the appearance of colors in gold solutions. Particles of gold in water makes the solution appear different colors when viewed directly or obliquely; it can appear red directly and blue obliquely because of the difference in scattering and absorption. Mie derived a solution for perfect spheres in a liquid media. The solution involves the slow conversion of complicated functions. Even though it was originally developed to explain particle behavior in water, it is almost always applied to air media problems—principally water droplets in air and intergalactic particles in air. This formulation has been generalized for dielectric spheres (such as water droplets) and other particle shapes such as cylinders and spheroids. Analytical solutions are only available for special cases such as spherical or cylindrical particles in cases where the particle refractive index is only marginally higher than that of the media; a condition approximated by blood.

Figure 4:
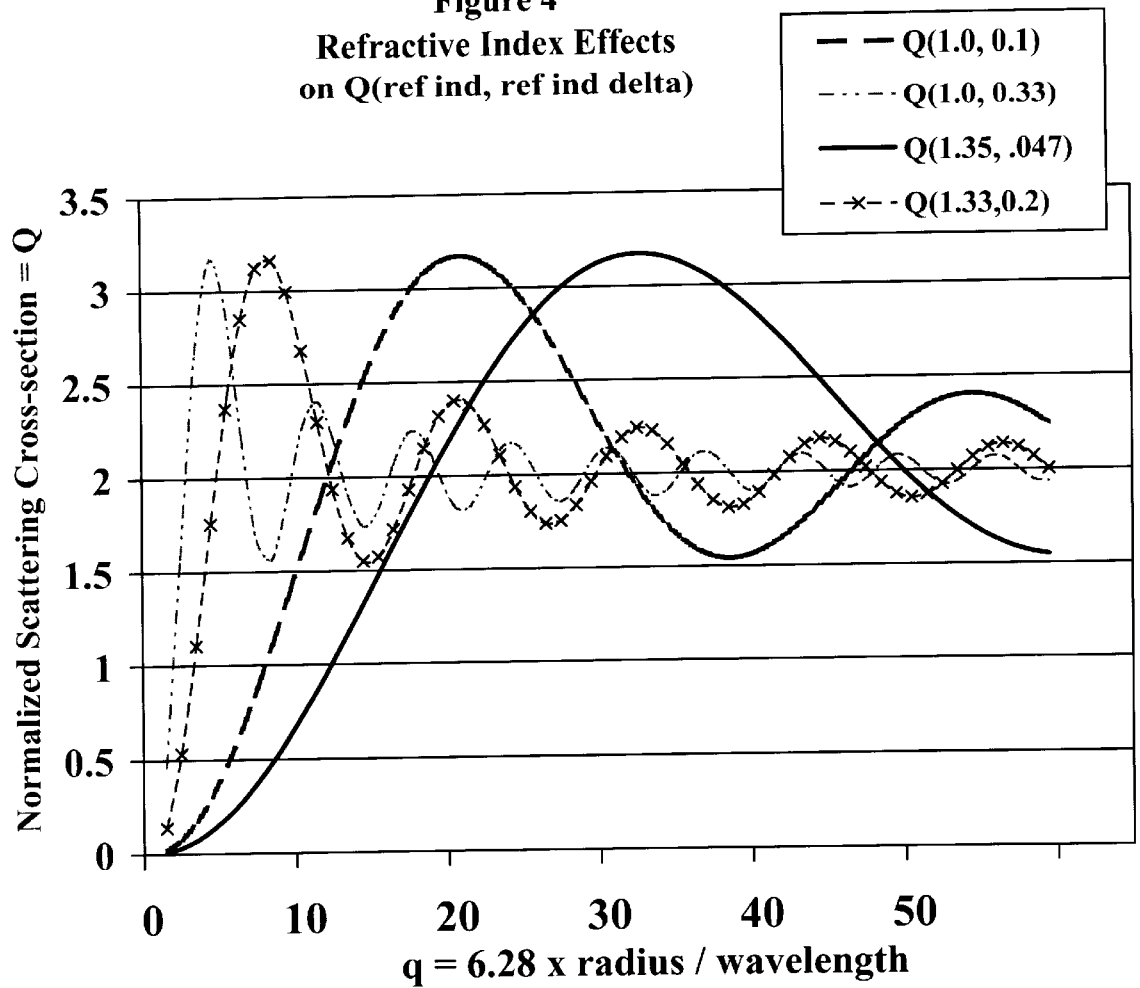
FIG. 4 is a graph of the normalized scattering cross-section versus q for different refractive indices.

The principle application of Mie scattering is in observing objects in air through particulates such as haze and fog whose particulate size range from 0.1–10 microns. The classic application is visualizing structures through haze or fog. Haze or fog consists of spherical water droplets with diameters varying from sub-micron levels (ground haze) to 10 microns (dense fog). Mathematical solutions to this problem reveal why near-infrared penetrates ground haze.[3] (FIG. 4). Scattering is quantified by calculating the total scattering cross-section Q of a group of particles normal to the light beam. The scattering cross-section is actually larger than the physical cross-section for most wavelengths; for most wavelengths it is twice the physical cross-section reaching a peak of 3–4 times the physical cross-section depending on the relative refractive index. This ratio of scattering cross-section divided by the physical cross-section is called the normalized scattering cross-section for a group of particles of radius a: $Q(norm)=Q/\pi a^2$. This quantity represents the effective scattering area as compared to the physical cross-section.

As wavelength lengthens to a value comparable to particle radius, Q reaches a peak, followed by a rapid decline in scattering. From FIG. 4 note the normalized scattering cross-section is plotted versus q; a measure of the ratio of wavelength to particle radius. The variable q is defined as:

$$q=2\pi a/\lambda \qquad \text{Equation 3}$$

This is the ratio of the particle circumference to the wavelength. It is noted that the normalized scattering cross-section Q(norm) reaches a maximum of four at q=6 and values approaching zero at q<1. Particles with radii and wavelengths corresponding to a q=6 will have maximum scattering. For a given particle size, as wavelength lengthens from this point, the scattering cross-section shrinks on the order of $(1/\lambda)$.

This condition is filled when looking at distant objects through surface haze. Haze consists of water droplets about 0.2–1.0 microns in radius suspended in air. Particles are larger early in the morning and gradually decrease in size as the sun heats them. The wavelength corresponding to these conditions (a=0.3–1.0 and q=6) is 0.31–1.05 microns. Recalling that the visible spectrum is 0.4–0.75 microns, visibility characteristics through surface haze are explained by FIG. 3. Early morning surface haze has larger-radius particles—around 1.0 microns. Maximum scattering would occur at a wavelength of 1.05 microns; the near-infrared. The visible wavelengths of 0.45–0.75 microns correspond to q=8.4–14.0. In this q range, the normalized scattering cross-section Q(norm) is between 2–3. Particles appear 2–3 times their physical size explaining the difficulty in seeing objects through early morning haze. Conversely, at q=3, the normalized scattering cross-section is halved to a value of two. The particles at this wavelength appear half the size (from a scattering point of view) than do particles when q=6. Visibility will be much improved. The wavelength for which q=3 is 1.04 microns; a wavelength in the near-infrared. This explains the success of near-infrared satellite cameras in penetrating ground haze. As wavelength increases, the scattering cross-section reduces allowing greater visibility.

Figure 3:
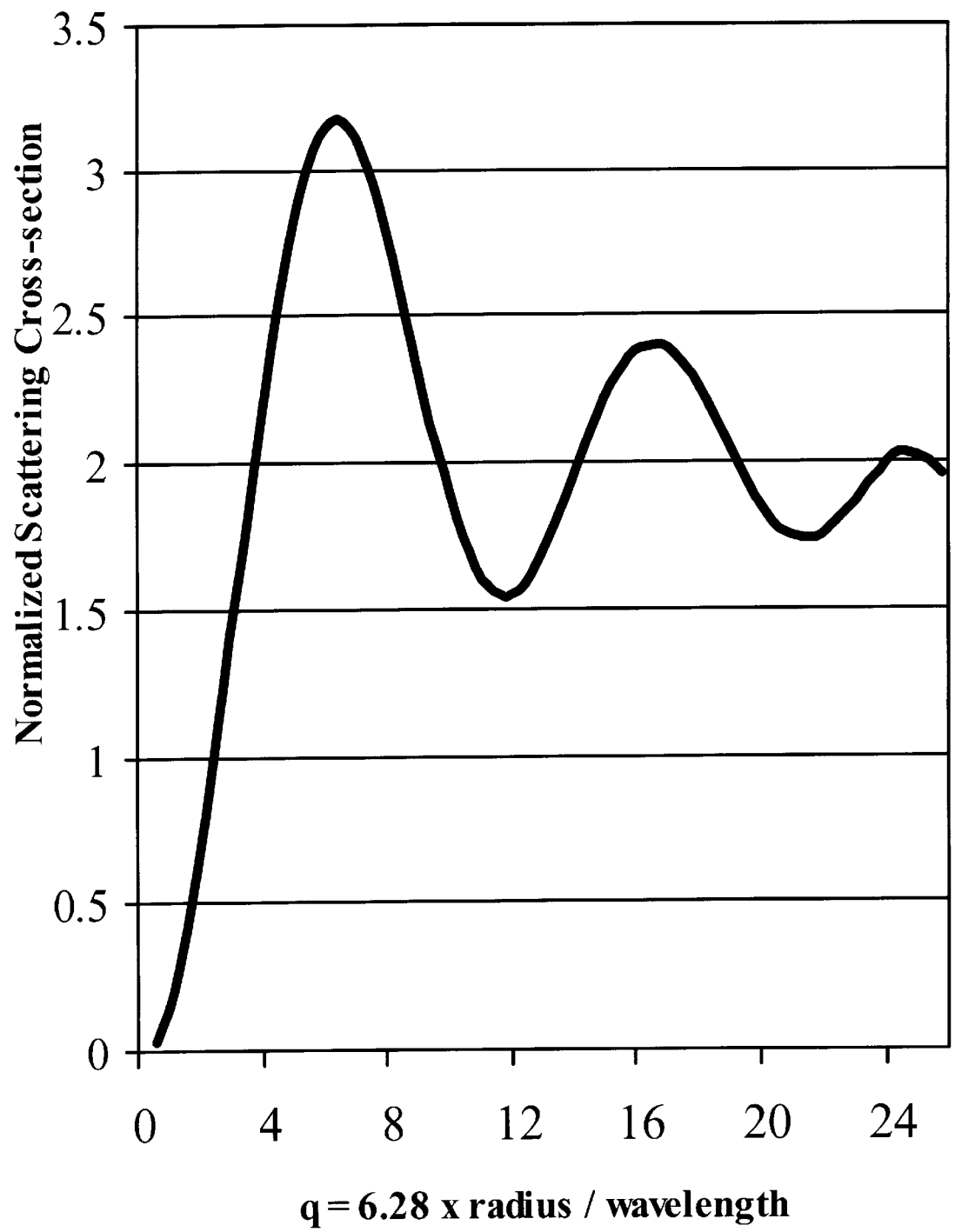
FIG. 3 is a graph of the normalized scattering cross-section versus $q=2\pi a/\lambda$ for water droplets in air.

The smallest particle radii (a=0.2) would correspond to a q-range of 1.6–2.7 for visible wavelengths. Referring to FIG. 4 [check], the normalized scattering cross-section Q(norm) is smaller—about 0.5–1.2. These particles scatter as particles only half to slightly more than their size. On a micron level, the particles at 0.5 microns with surface area 0.79 square microns appear 2–3 times larger or 1.6–2.4 square micron particles, from a scattering point of view. Particles at 0.2 microns (area=0.13 square microns) scatter if they were 0.07–1.56 square micron areas. At lower radii, the normalized scattering cross-section becomes very small. At a certain point, the particles are practically invisible. For water vapor (refractive index 1.33 in a medium of 1.00), FIG. 3 shows for a value of q=1, the normalized scattering cross-section to be near zero; the particles have only tiny cross-sections. This condition is observed at the point when haze appears to vanish. In fact, the water droplets have now reduced to a size where q is around unity. In the middle of the visible spectrum $\lambda$=0.6 microns. The droplet radius for this condition is determined by solving Equation 3 for a:

$$a=\lambda/(2\pi)=0.1 \text{ microns} \quad \text{Equation 4}$$

Thus, particles with radius lower than one-tenth of a micron do not interfere with long-distance viewing The peak value of q is specific to water droplets in the atmosphere since water particles and air have certain indices of refraction: 1 for air, 1.33 for the water droplet. Particles and media with different indices of refraction will have the scattering maximum at different values of q. Water-based paint is an example of a larger refractive index difference. One of the few areas in the literature where scattering properties in fluids are considered is in paint manufacturing. Paint consists of zinc-oxide particles suspended in water; where the refractive index difference between pigment—water is greater than in water droplets—air. In paint, it is desirable to have the scattering peak in various areas in the visible spectrum to create maximum brightness. A well-known maxim in the paint industry is to use particles with diameters about ½ the average wavelength of visible light; or about 0.25 microns. With these particle diameters a light scattering maximum is achieved and the painted surface appears brightest. Clewell (see references) investigated this application in 1941, and developed an empirical mathematical model of this phenomenon based on Mie Scattering Principles.

In this case, the media index of refraction defined as (n) is 1.33 for water instead of 1 for air. Light travels slower in media where the media index of refraction n>1 shortening the wavelength to $\lambda/n$, where $\lambda$ is the wavelength in air. Thus, the more general expression for q is $$q=2\pi an/\lambda \quad \text{Equation 5}$$

Equation 6 is used when the media is not air to calculate values of q that correspond to the maxim of using particles half the visible spectrum wavelength. If the scattering maximum is reached for a particle diameter at ½ the wavelength ($\lambda$) for a particle of radius (a) in a media of refractive index (n=1.33) then 2a=½$\lambda$ or a/$\lambda$=0.25. The value for q at this point is $$q=2\pi na/\lambda=2(3.14)(1.33)(0.25)=2.1. \quad \text{Equation 6}$$

Clewell shows experimental curves for paint which demonstrate a scattering maximum centered at about 2.9; a result in general agreement with the maxim. Thus, the value of q at the scattering maximum is close to three instead of six as in water vapor; a result due to differences in refractive index. Water particles are non-conductive with a relative refractive index of 0.33. Paint particles are metallic with a complex refractive index higher than water vapor. Red blood cells suspended in plasma is an example of a very small differential refractive index; a differential of only 0.064.

Figure 5:
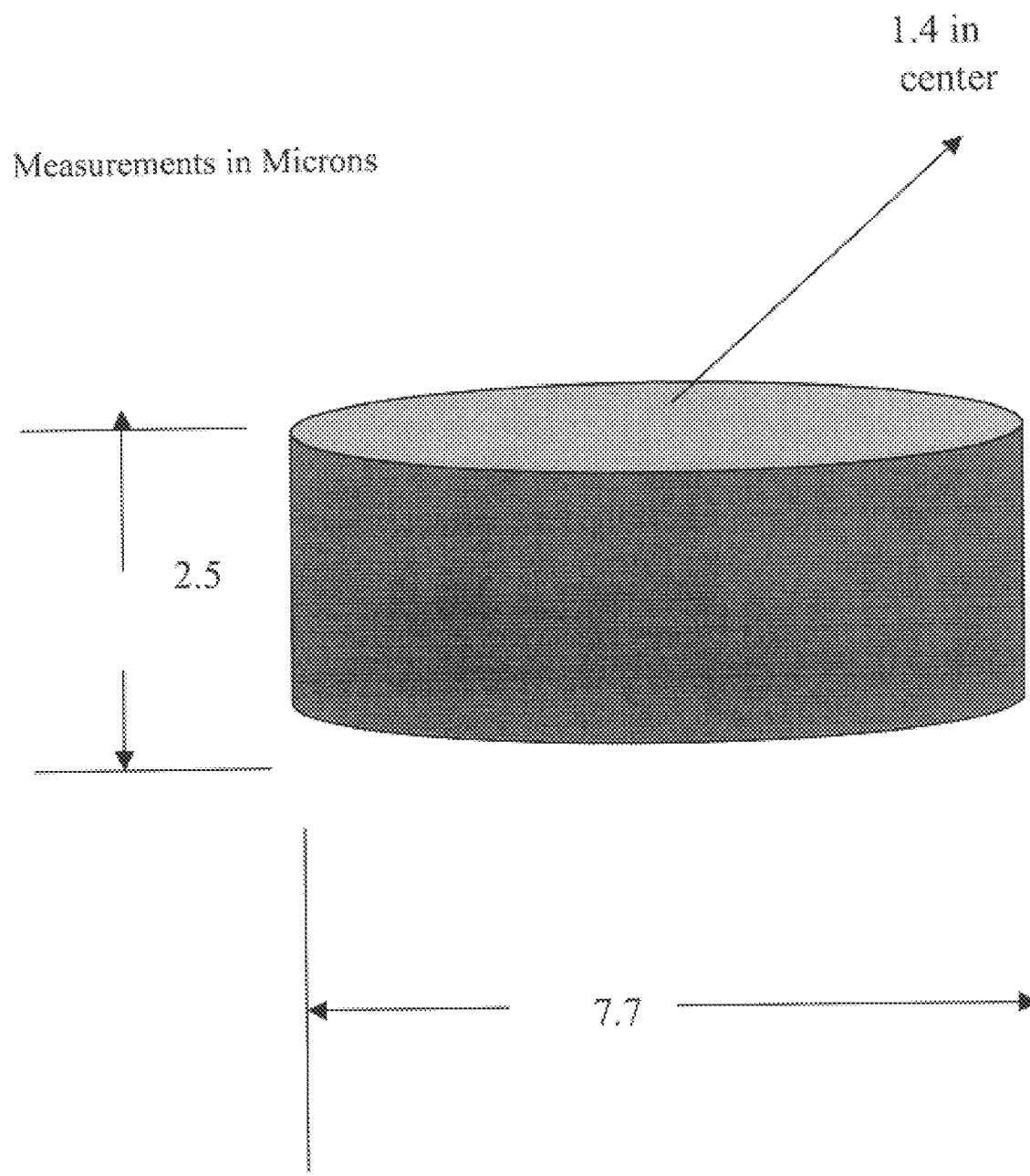
FIG. 5 is a picture of red blood cell with relevant dimensions.

Van de Hulst derives a more general curve for particles of arbitrary relative refractive index (FIG. 5). For n=1.5, the maximum occurs at q=4. When n=1.33, this value shifts to q=6; the familiar water vapor example. The scattering curves for these particles show scattering maximums at higher values of q as refractive index decreases. (FIG. 4). Note that as wavelength lengthens (q decreases) from this point, the scattering cross-section shrinks towards values much smaller than the actual physical cross-section. To determine this region for blood the equivalent sphere size and the refractive index need to be known.

C. VAN DE HULST THEORY FOR SMALL RELATIVE REFRACTIVE INDEX

The situation where the relative refractive index is small is one of the major simplifying conditions in the Mie Theory. Van de Hulst in "Scattering by Small Particles" (see references) has derived the equation for the normalized scattering cross-section:

$$Q(\text{norm})=2-(4/\rho)\sin \pi+(4/\rho^2)(1-\cos \rho) \quad \text{Equation 7}$$

Where $$\rho=2q\delta \quad \text{Equation 8}$$

$$\delta=[n(\text{particle})-n(\text{media})]/n(\text{media}).=\Delta n/n(\text{media}) \quad \text{Equation 9}$$

Figure 6:
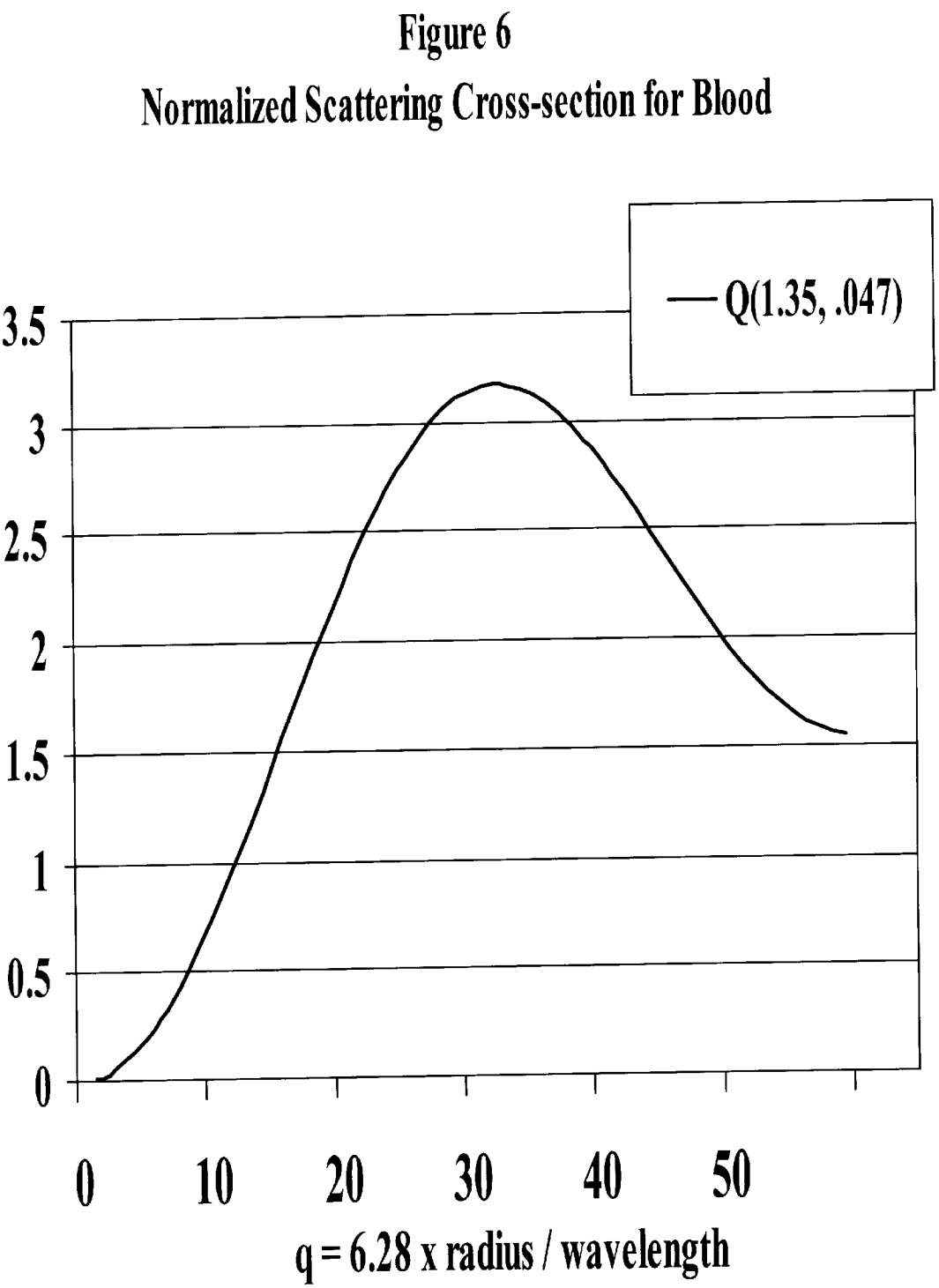
FIG. 6 is a graph of the normalized scattering cross-section versus q for blood.

Note the absorption is no longer q but the parameter $\rho$. Equation 7 is plotted in FIG. 6. As can be seen in FIG. 6, peak scattering occurs for $\rho$=4 where the normalized scattering cross-section is 3.18. These results apply to particle suspensions with marginally higher particle refractive index. For larger differential refractive indices, the normalized scattering cross-section increases towards a value of four, but the scattering maximum point remains at the same value of $\rho$=4. Solving Equation 7 for $\rho$=4 yields:

$$q=2/\delta. \quad \text{Equation 10}$$

Equation 10 even applies to larger refractive index differences such as water vapor where $\delta$=0.33. This value yields a scattering maximum expected to occur at q=6.11; a result in close agreement with the experimental water vapor maximum of q=6 shown in FIG. 3.

The value of q for the scattering maximum in red blood cells can be calculated since the red blood cell refractive index is known—$\delta$ can be calculated. More importantly, Equation 7 can be used to calculate the expected wavelength dependence for blood modeled as spheres of given radius and refractive index. The radius, refractive index of the particles and the refractive index of the media corresponding will now be calculated culminating in a prediction of distance seen through blood versus wavelength.

D. RED BLOOD CELL SIZE

Red blood cells constitute approximately 95% of the mass floating in plasma. Other entities such as white blood cells and platelets take up the remainder. Visible light cannot transmit through blood because the absorption and scattering cross-section of the red blood cells is too large. Blood cannot be seen through because of the red blood cells. To determine the proper spherical radius and indices of refraction, the physical nature of the red blood cell needs to be examined. Red blood cells, in fact, are bio-concave disks about 7.7 microns in diameter, with a thickness ranging from about 1.4 microns in the center to about 2.5 microns along the edges (FIG. 5). Optical measurements measure its sphericity as 0.77 with 1.00 being a perfect sphere. Consequently, red blood cells can be modeled as spherical particles between the extremes of d=7.7, a=3.85 microns and d=1.4, a=0.70 microns—corresponding to the longest and shortest dimensions of the cell. Thus it is expected that a red blood cell will correspond to a spheres with radii between 0.70–3.85 microns—likely around 2. FIG. 6 show the scattering cross-section for blood versus wavelength of spheres with radii between 1.0 and 3.85 microns. Note that larger spheres have their scattering cross-section decrease more slowly with lengthening wavelength. Nonetheless, even for the largest sphere, the reduction in scattering cross-section is significant throughout the infrared wavelength region. Later in this section, it is shown that the scattering cross-section of red blood cells behaves like spheres about 2.0 microns in radius. The remaining unspecified variables to calculate are the indices of refraction.

E. BLOOD REFRACTIVE INDEX

All biological cells are remarkably consistent is their refractive index. The refractive index for a cell in aqueous media is expressed as $$n(\text{cell}) = n(\text{media}) + \beta c \qquad \text{Equation 11}$$

where β is a constant for biological cells having a range of 0.00180–00185 and c is the concentration in gms/deciliter. The average red blood cell has a concentration c=29–39 gms/deciliter. Using the midpoints of these values, the red blood cell has a slightly higher refractive index than plasma of $$\Delta n = n(\text{media}) - n(\text{cell}) = 0.064 \qquad \text{Equation 12}$$

The scattering cross-section for blood modeled as spheres versus q can now be calculated from the refractive indices for red blood cells and plasma. Plasma consists of water, protein (7%, n=1.4) inorganic ash (0.95%, n=1.5), lipids (0.80%, n=1.4). The overall refractive index is a weighted average of these indices of $$n(\text{media}) = 1.35 \qquad \text{Equation 13}$$

Now δ can be calculated:

$$\delta = \Delta n / n(\text{media}) = 0.064/1.35 = 0.0474 \qquad \text{Equation 14}$$

Inserting this value in Equation 10, yields the scattering maximum for blood at:

$$q = 2/0.0474 = 42.19. \qquad \text{Equation 15}$$

Rearranging Equation 5, maximum scattering occurs in the middle of visible wavelengths (using a mean Mie-sphere radius of 3.85 microns for the red blood cell) of $$\lambda = 2\pi a n / q = 0.57 \text{ microns} \qquad \text{Equation 16}$$

F. SCATTERING CROSS-SECTION FORMULA FOR BLOOD

The entire scattering curve can be calculated as a function of q since $$\rho = 2q\delta = 0.095 q \qquad \text{Equation 17}$$

Solving for Q(norm) with this value of yields the equation for blood relating normalized scattering cross-section to q:

$$Q(\text{norm}) = 2 - (4/\rho)\sin \rho + (4/\rho^2)(1 - \cos \rho) \qquad \text{Equation 18}$$

Equations 17 and 18 describe the normalized scattering cross-sectional area for red blood cells modeled as spheres and is graphed in FIG. 5. Note maximum scattering takes place at q=42.19, followed by a rapid decline in scattering cross-section. When radius equals wavelength, scattering cross-section is only 0.32—down from the maximum at 3.16 square microns. For wavelengths three times larger than the radius, the scattering cross-section is only 0.035 sq microns or about 1% of the maximum scattering cross-section cells.

As the red blood cells shrink in scattering cross-section, greater distances will be seen through blood. In this region, Equation 17 can be simplified using a Taylor's Series expansion. For ρ<<1, $$Q(\text{norm}) = \rho^2/2 \qquad \text{Equation 19}$$

Substituting ρ=0.095q $$Q(\text{norm}) = 0.0047 q^2 \qquad \text{Equation 20}$$

Or since q=2π (a/λ)n(media)

$$Q(\text{norm}) = 0.32 (a/\lambda)^2 \qquad \text{Equation 21}$$

So for small a/λ, scattering cross-sections for spheres of radius 'a' shrink rapidly as inverse as the square of the wavelength. Equation 21 describes the shrinkage of scattering cross-section with wavelength in this regime.

Figure 7:
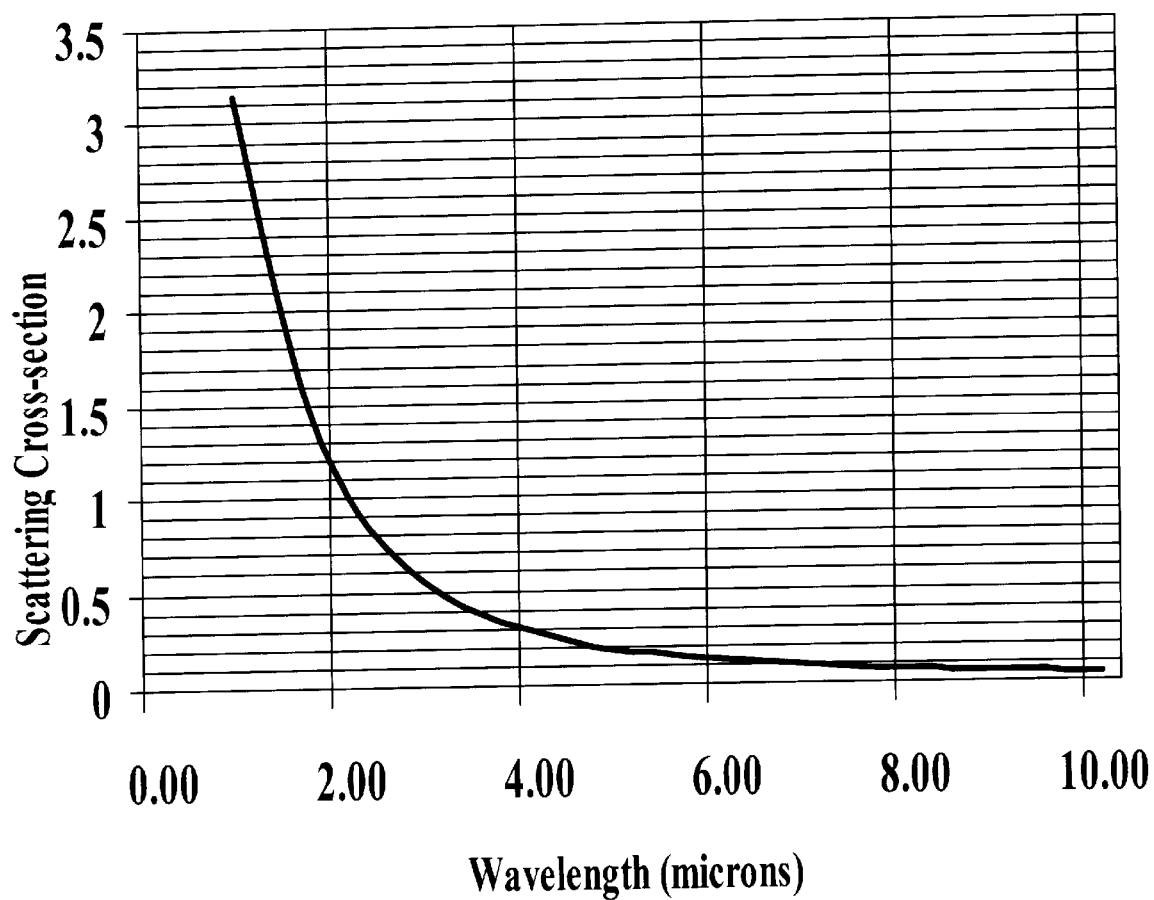
FIG. 7 is a graph of the normalized scattering cross-section versus wavelength for blood.
Figure 8:
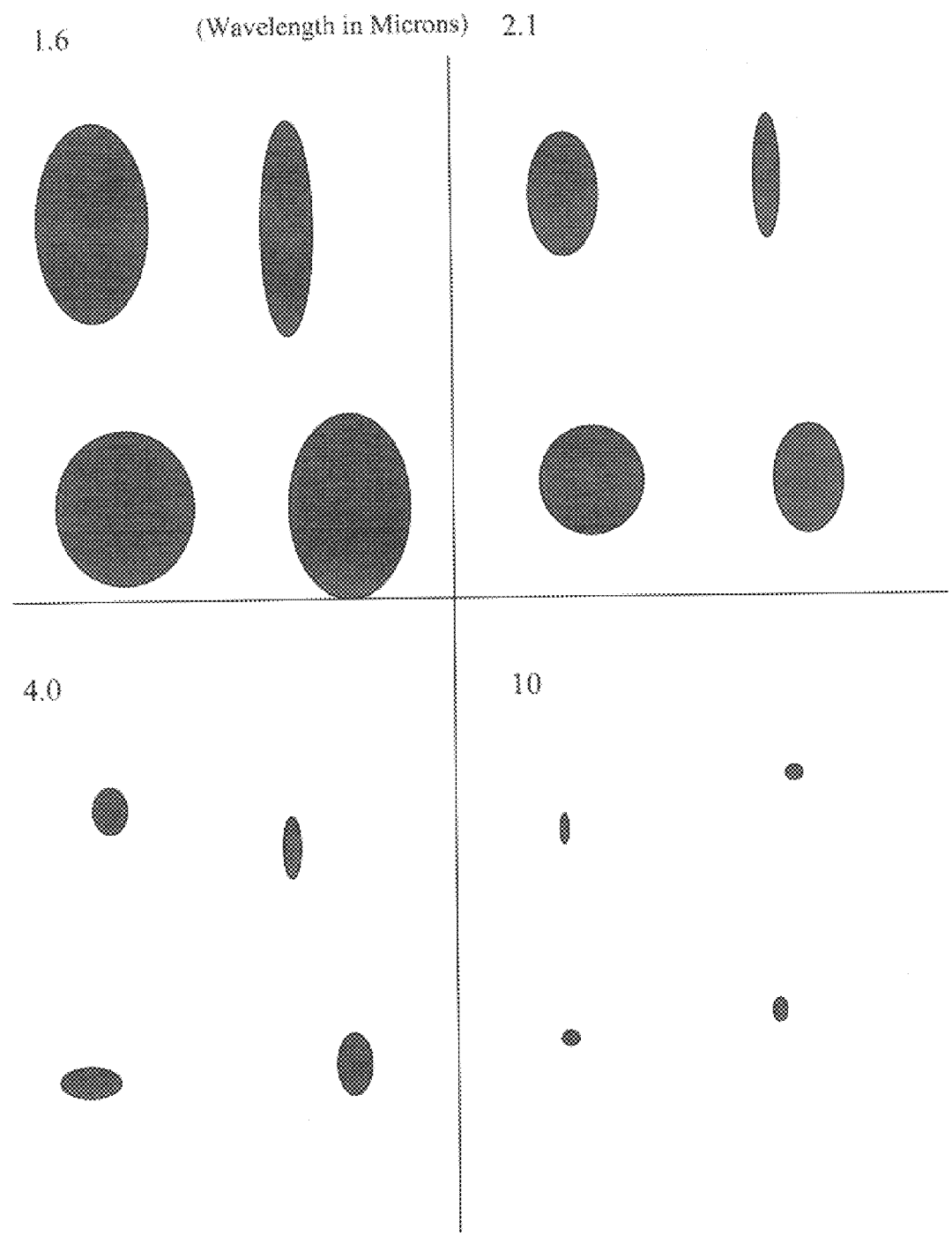
FIG. 8 is a two-dimensional view of the size of red blood cells at the illuminating wavelengths 1.6, 2.1, 4.0 and 10 microns.

Scattering cross-section decreases very rapidly with wavelength. FIG. 8 demonstrates the large reduction in normalized scattering cross-section at wavelengths 1.6, 2.1, 4.0 and 10 microns. A principle teaching herein is that scattering cross-section for red blood cells in plasma is significantly reduced for wavelengths exceeding 1.4 microns. In FIG. 7, the advantage of reducing scattering by increasing wavelength can be readily appreciated. The scattering maximum of 3.12 occurs at a wavelength of 0.7 microns—a wavelength in the high end of the visible spectrum. At a wavelength of 1.4 microns, the normalized scattering cross-section has reduced to 1.88. At 2.2 microns, the cross-section has shrunk almost in half from its value at 1.4 microns—to a value of 0.98. At 4.0 microns, the normalized scattering cross-section is only 0.29. Thus scattering cross-sections at a 4.0-micron illuminating wavelength are less than one-tenth of the their value at 0.7 microns.

While the Mie Theory provides an approximate guide to finding the wavelengths where scattering cross-section decreases, the assumptions are different enough to require experimental verification. Red blood cells in plasma satisfy the criteria of marginal refractive index much better than water vapor. Two conditions not satisfied are the assumptions that the particles are spherical; they are in fact bio-concave discs and that the particles are separated at a distance much greater than the wavelength. The former is dealt with below as a modification to the theory. This last condition is applied to ignore multiple scattering which make the problem unsolvable. Previously it was shown that Mie Scattering principles even apply to dense liquid suspensions such as paint. Compared to paint, red blood cells in plasma have little primary scattering because of the small difference in the refractive index and therefore would have reduced multi-scattering as well. Also, unlike most particle suspensions described in the literature, red blood cells in a given individual are very homogenous; they all have a similar size. Metallic particles or air droplets vary in size to a much greater degree—usually by an order of magnitude. Particles of the same size would have a sharper wavelength point at which scattering decreases rather than a more dispersive region seen in suspensions in the literature. The exact response of red blood cells need to be determined experimentally both to verify the above theory and to determine viewing distance of structures immersed in blood as a function of scattering cross-section.

EXPERIMENTS INTRODUCTION

Orthoscope contains ports for the exit of illumination and collection fibers. Various laser diode light sources were connected to the illumination fiber port, while the camera, containing focusing lenses, was connected to the collection fibers. This assembly was inserted in circulating blood until it touched the target at which point it would be slowly withdrawn until the target was no longer resolvable. Targets consisted of 12 font print on white paper and tubes ranging from 2–4 mm diameter. The distance limit defined as 'l', is defined as the distance through blood at which the image becomes unrecognizable. The error of this measurement is 0.25 millimeters.

Absorption and scattering have different characteristics when viewing structures in blood. High scattering manifests itself as a loss of image resolution until the structure is unrecognizable even though sufficient light is present to illuminate the structure. High absorption appears as insufficient illumination. Observing when the light decreases to a value too dim for the camera to register an image is a measure of the combined absorption of water and hemoglobin.

To determine the relationship between scattering cross-section and viewable distance, a series of measurements were conducted by diluting blood with water at varying dilutions at a fixed near-infrared wavelength. Mie Theory teaches that the degree of overall scattering is proportional to the total scattering extinction cross-section $$\sigma = NQ\pi a^2 \qquad \text{Equation 25}$$

where N is the number of particle and "Q" is the individual normalized cross-section and "a" is the Mie-sphere radius. The total scattering cross-section (coherent scattering cross-section) measured in the experiments is similar, but different. Extinction cross-section refers to scattered light in all directions; coherent scattering cross-section refers to light only minimally scattered and therefore useful in registering resolvable images. Coherent scattering cross-section is also proportional to Q and N. Consequently, changing either variable can reduce total coherent scattering cross-section.

This relationship needs to be determined experimentally since it relates to the density and shape of the particulates. Dilution reduces the overall scattering cross-section in proportion to the dilution. For example a 1:1 water-blood dilution corresponds to half the scattering cross-section of undiluted blood; four parts water to one part blood corresponds to a quarter of the overall scattering cross-section of undiluted blood. Conversely, the same effect can be achieved by employing illuminating wavelengths—which reduces Q by 50% or 25%—leaving N unchanged. Thus the total coherent scattering cross-section can be reduced by changing the number of particles or by increasing the illuminating wavelength.

EXPERIMENTS DATA

Experiments were conducted with wavelengths from the visible (0.5 microns) to the mid-infrared (1.6 microns). The wavelengths considered were visible, 0.50, 0.65, 0.88, 0.95, 1.00, 1.35 and 1.6 microns. All of these wavelengths were tested first in a test solution consisting of tomato juice and then tested in whole, fresh human blood. Tomato juice was used as the test solution since it consists primarily of suspended cells from the tomato plant. Since biological cells are approximately of ten-micron diameter range and are only marginally higher in refractive index depending on their protein content, the theory developed above applies to tomato juice as well as blood. Experiments demonstrated structures could be viewed through tomato juice about twice as far as blood regardless of wavelength; indicating that the scattering particles are of similar size to the red blood cell, but are present in reduced concentration.

With blood, the effect of the various wavelength light sources is as follows. Since hemoglobin reaches a minimum at about 0.8 microns, the light source with wavelength 0.88 microns and above are near the lowest hemoglobin absorption—where enhanced viewing distances are expected. The largest wavelengths (1.35 and 1.6 microns) are sufficiently long to observe the scattering cross-section shrinking predicted in the Mie Theory as well as the absorption of water. For wavelengths starting at 1.0 micron, the camera needed to be changed to one sensitive to infrared light. The light sources were of fixed intensity ranging from 2–10 milliwatts. The blood was donated from a single human individual and contained a minimal amount of heparin to prevent clotting.

Visible Wavelengths

Experiments began with the visible spectrum where measurements were made monochromatic laser diodes with wavelengths 0.5 and 0.65—both in the visible spectrum (0.45–0.75 microns). The light sources has intensities of 30 and 45 milliwatts respectively. Structures could only be visualized through blood only at small distances—about 0.6 millimeter. Visible light, ironically, is the poorest wavelength to "see through" blood.

0.88–1.0 Microns

The next experiments used illuminating wavelengths in the near-infrared: 0.88, 0.95 and 1.0 microns. Wavelengths in this region require smaller wattage light sources since hemoglobin absorption reaches its minimum in this wavelength region. Light wattages were 20, 25 and 15 milliwatts, respectively. The camera was a CCD camera sensitive to the near-infrared.

At 0.88 microns, a measurable viewing distance of 1 mm is achieved. At this point there is still sufficient light present to view an image but the image is not resolvable. As discussed in the hemoglobin absorption section above and seen in FIG. 2, hemoglobin absorption reaches a minimum of about 5–10 (1/cm) at this wavelength. Water in this region is virtually transparent with negligible absorption so Equation 1 applies to this situation. At 0.95 microns, l increases slightly to about 1.2 microns. The 1.0-micron wavelength illuminating light source also has an l of 1.2 microns 1.35 and 1.60 Microns In these experiments, 1.35 and 1.60 micron wavelength sources were used with the infrared camera. In this region, hemoglobin absorption remains at a minimum, while water absorption becomes apparent. The intensities were 5 milliwatts for the 1.35-micron source and 8 milliwatts for the 1.6-micron source. These intensities were adequate for the short viewing distance seen with the 1.35-micron wavelength source. The 1.6-micron source light intensity was only marginally adequate at the longest viewing distances. Resolvable images could still be discerned when the illumination became insufficient.

The 1.35-micron source produced improved maximum viewing distances significantly to 1.75–2.25 mm with an average of 2.00 mm. At that point, there was still sufficient light to view images, so this limitation in distance is due to scattering. The 1.6 micron source resulted in a much greater distance of 4.0–4.5 mm with an average of 4.25 mm. At a distance of 2 mm, none of the targets were visible at a 1.35-micron wavelength, while they could be clearly seen at a 1.6-micron wavelength. These results are summarized in Table 3.

TABLE 3

| λ (microns) | l (mm) in blood | l (mm) in tomato juice |
|---|---|---|
| 0.5, 0.65 | 0.6 | 1.5 |
| 0.88 | 1.0 | 2.0 |
| 0.95 | 1.25 | 2.5 |
| 1.0 | 1.25 | 2.6 |
| 1.35 | 2.0 | 3.9 |
| 1.6 | 4.25 | 8.3 |

To determine the relationship between viewing distance and scattering cross-section, a series of measurements were made with the 0.88 micron light source and blood of varying dilutions. This wavelength was chosen since it is at the point where the absorption by hemoglobin has reached its minimum. Dilutions ranging from two parts blood, one part water to four parts water: one part blood were used in the experiment. If dilutions are expressed as a percentage of red blood cells as compared to undiluted blood, the following dilutions were considered: 100%, 66%, 50%, 33% and 25%. Table 4 summarizes the data showing the viewable distance versus dilution percentage.

TABLE 4

| Dilution Percentage (%) | Viewing Distance (millimeters) |
|---|---|
| 100 | 1.0 |
| 66 | 2.4 |
| 50 | 4.1 |
| 33 | 11.8 |
| 25 | 18.5 |

EXPERIMENTS DISCUSSION

Figure 9:
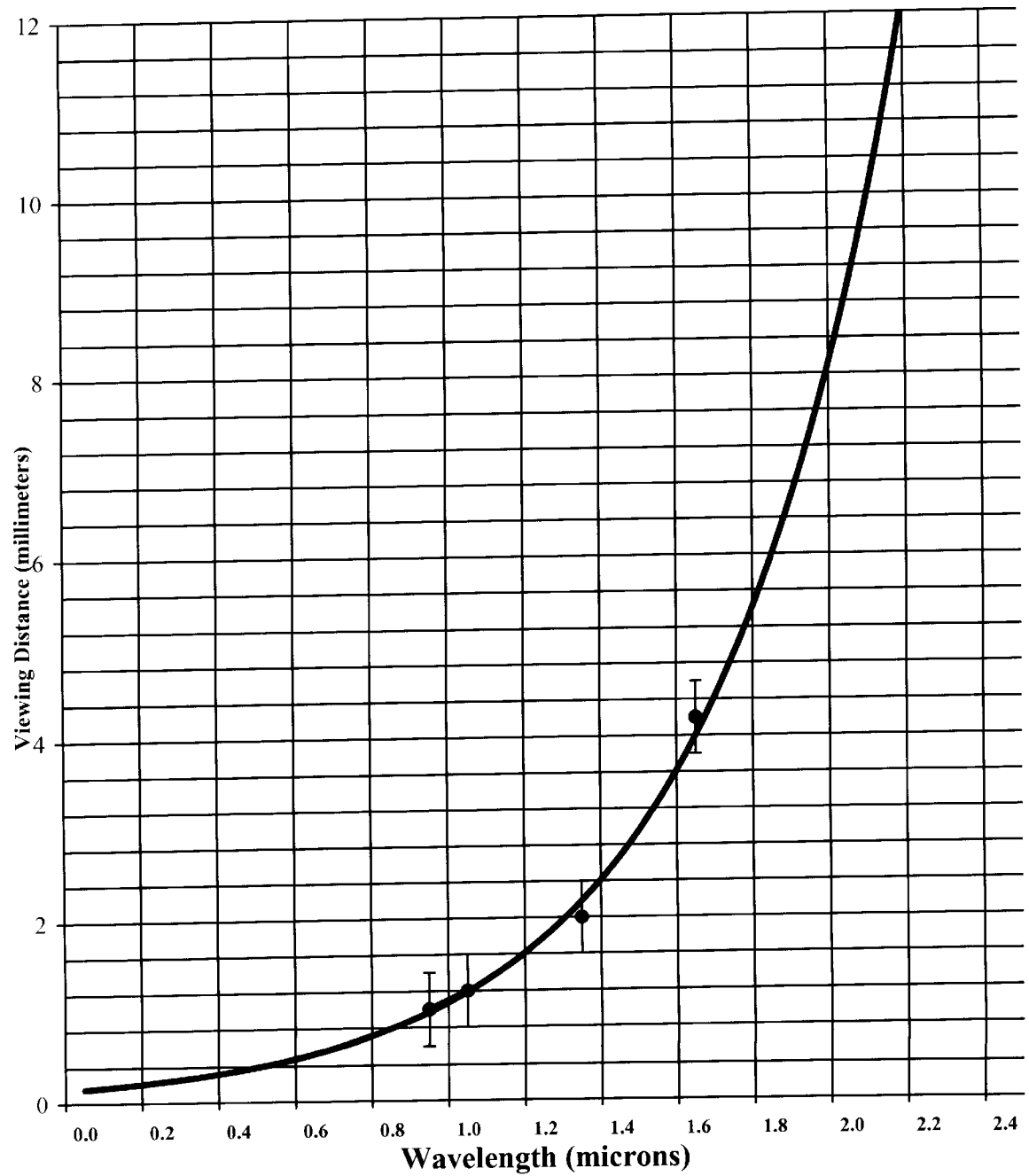
FIG. 9 is a graph of coherent viewing distance versus scattering cross-section. Dashed line is the data for total cross-section reduced by dilution. Solid line is data for cross-section reduced by increasing wavelength. The total cross-section is also expressed as an equivalent wavelength for a 2.2-micron Mie-sphere and an equivalent blood-water dilution. A dot and an error bar indicate data points at different wavelengths.

These data from these experiments is presented in FIG. 9. FIG. 9 shows the total coherent scattering cross-section versus viewing distance l. For a given Mie-sphere radius, the total coherent scattering cross-section is calculated using Equations 17, 18 for each of the illuminating light wavelengths.

TABLE 5

| Wavelength (microns) | Q(norm) for 3-micron sphere | Q(norm) for 3.85-micron sphere | Q(norm) for 4-micron sphere |
|---|---|---|---|
| 0.6 | 3.17 | 2.81 | 2.68 |
| 0.88 | 2.38 | 3.00 | 3.06 |
| 1.35 | 1.28 | 1.89 | 2.00 |
| 1.6 | 0.96 | 1.46 | 1.55 |
| 2.1 | 0.59 | 0.92 | 0.99 |
| 2.4 | 0.46 | 0.73 | 0.78 |
| 4.0 | 0.17 | 0.28 | 0.30 |
| 5.0 | 0.11 | 0.18 | 0.19 |
| 10 | 0.03 | 0.04 | 0.05 |

Note that the total normalized coherent-scattering cross-section changes differently versus wavelength for each of the sphere radii. Since the dilution experiment specifies the viewing distance for each total coherent scattering, the appropriate-sized sphere can be inferred from the experimental data. The dilution data is indicated with a dashed line. For example, comparing the 0.88-micron wavelength to the 1.6-micron wavelength data, the viewable distance is increased from 1.0 to 4.25 millimeters. From the dilution data (Table 4), this same increase in viewing distance occurs for a dilution of 50%; or when the scattering cross-section is reduced by a factor of two. As seen in Table 5, the 3.85-micron Mie-sphere model is the approximate radius, which predicts a halving of cross-section from 0.88 microns to 1.6 microns. The 3.85 sphere radius predicted from the wavelength behavior seen in the experiments agrees with the physical evidence: the diameter of a red blood cell is 7.7 microns. If the red blood cells behaved as a 3.0-radius sphere, a longer viewing distance would have been observed at 1.6 microns, since the scattering cross-section is reduced by more than half. Conversely, a 4.0-micron radius sphere would have a shorter viewable distance since the cross-section is reduced by less than half. FIG. 9 demonstrates similar close agreement for the 3.85-micron radius sphere for the other wavelengths. As seen in FIG. 9, considerably longer viewing distances are achieved when the illuminating wavelength lengthens. FIG. 9 shows the experimental measurements compared to results predicted with a 3.85-micron radius sphere. Note the closeness with which the experimental results agree with theory. Table 4 indicates a viewing distance of over 11 millimeters when the total cross-section is reduced 33% from undiluted blood. As seen in Table 5, total scattering cross-section for the 3.85-micron radius sphere at a 2.1-micron wavelength is reduced 31% from the cross-section at wavelength 0.88 microns. Consequently, a viewing distance of over 11 millimeters is expected when a 2.1-micron wavelength is employed. Similarly, for a 25% dilution, a viewing distance of over 18 millimeters is achievable with light at a 0.88-micron wavelength. Since the normalized cross-section is 3.00 for the 0.88-micron wavelength, a 25% dilution corresponds to a cross-section of 0.75. Approximately the same cross-section occurs for light at 2.4 microns. Thus a 25% reduction in cross-section would occur at a wavelength of about 2.4 microns, corresponding to a viewing distance of over 18 millimeters. Table 6 compares the experimental data to predicted results based on the cross-section reduction measured from the dilution experiment (Table 4)

TABLE 6

| Wavelength (microns) | Normalized Scattering Cross-section for 3.85-micron Sphere | Equivalent Dilution Percentage | Viewing Distance through Blood Based on Dilution Meas. (millimeters) | Viewing Distance from Experiments (millimeters) |
|---|---|---|---|---|
| 0.88 | 3.00 | 100 | 1.0 | 1.0 |
| 1.35 | 1.89 | 63 | 2.3 | 2.0 |
| 1.60 | 1.46 | 49 | 3.8 | 4.25 |
| 2.10 | 0.92 | 31 | 9.5 | |
| 2.40 | 0.85 | 24 | 15.3 | |
| 4.00 | 0.28 | 9 | 93 | |
| 5.00 | 0.18 | 6 | 220 | |
| 10.00 | 0.05 | 2 | 3436 | |

Since a viewing distance through blood of 10–15 millimeters is sufficient to easily visualize structures inside a heart chamber, the 2.0–2.4-micron wavelength region is especially attractive. As discussed above in the absorption section, these wavelengths have an especially low absorption extinction coefficient of about 18 (1/cm). Consequently, low-intensity light sources in the watt-region can be utilized at this wavelength. The much longer distances expected for wavelengths 5 and 10 microns, are probably not achievable due to their higher absorption coefficients.

There are only certain wavelength regions locally semi-transparent to water. Each wavelength region requires different devices and materials as wavelength increases, resulting in different cameras, fiberoptic cable and lenses for optimal transmission and imaging. Since water has increasingly absorption with higher wavelength, more intense light sources are required. Consequently, the cost of the entire system increases substantially as wavelength increases. There are three regions where an infrared endoscope could operate efficiently.

FIG. 2 demonstrates five regions where water is locally semi-opaque. The first region is from wavelengths 1.4–1.8 microns. In this region the absorption of water is about (8.1/cm). Since scattering limits viewing for this wavelength to the half-centimeter range, a light source of about 10–30 milliwatts would illuminate that distance sufficiently to view structures. This wavelength would be useful for imaging structures in coronary arteries; a 5 millimeter viewing distance is more than adequate for a typical 3 millimeter diameter artery. Moreover, at this wavelength, cheaper cameras and smaller fiber-optic cables are available resulting in a cheaper system with a smaller fiber-optic cable.

The second region would extend following the large maxima at 1.8–2.0 microns from 2.1–2.4 microns where a typical water absorption extinction coefficient is about 18 (1/cm). From a scattering point of view, this region is anticipated to allow centimeter distance viewing. The actual true minimal absorption for a wavelength in this region is unknown for blood—but lower than for water, because of the debris in plasma. Using the worst case absorption extinction coefficient for water of 18 (1/cm), a light source of about one watt would be required to illuminate a region at a distance of 10 millimeters. Approximately one centimeter viewing would permit the infrared endoscope to be used within cardiac cambers in the heart. Examples include cardiac valve, septal defect and myocardial infarct inspection and viewing in-dwelling catheters. Furthermore, for vasculature application, the clarity of images in the coronary arteries would be improved at this wavelength compared to a wavelength in the 1.4–1.8-micron region.

The region between 3.8–4.2 microns has the lowest water absorption extinction coefficient—for wavelengths greater than 2.4 microns. From a scattering point of view, viewing distances of many centimeters are realizable with this wavelength region. In essence, there is a channel in the electromagnetic spectrum centered in this wavelength region—where water is semi-transparent. This region has a much larger absorption value in water of about 200 (1/cm). Since cells occupy 35% of the blood value, light travels through 35% hemoglobin and 65% water. Taking as average of these values suggest an overall absorption of (8+200)/2=104 (1/cm). Even this approximation is inadequate since blood cells often connect with each other (called Rouleaux formation) providing a low absorption pathway for light. The actual lowest measured absorption value for blood at this wavelength, and the intensity of the light source and the camera sensitivity will determine the peak viewable distance.

Large-wattage light output is possible using a flash configuration—light is only "on" for a very small percentage of time. The limitation in light source intensity is governed by the possibility of blood or tissue damage from the illuminating light beam. Conventional endoscopes use continuous light sources from 500–1000 watts. Much higher wattage can be achieved by pulsing the laser or laser diode synchronous with the cardiac rhythm. For the infrared endoscope, flashes of 1–10 microseconds are all that is required to register an image. Pulses of this duration will create local heating in only a micron-region from the tip of the infrared endoscope catheter. Consequently lasers or laser diodes, from a tissue-damage point-of-view, may operate with very high wattage. The upper wattage limit is governed, instead, by practical considerations, cost, size of illuminating device and power requirements.

FIRST EMBODIMENT
Coronary Artery Application

Figure 11A:
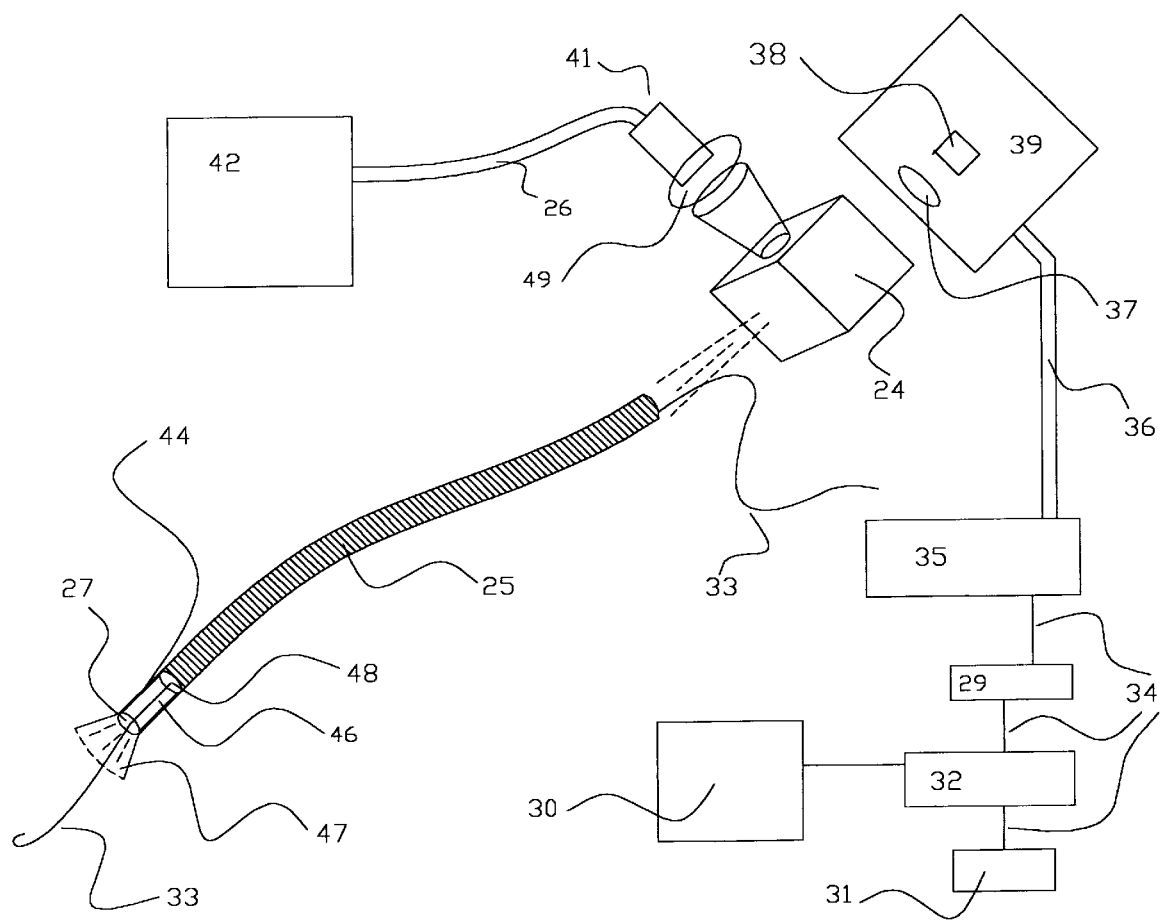
FIG. 11A depicts a view of the infrared endoscope system for coronary artery application.
Figure 11B:
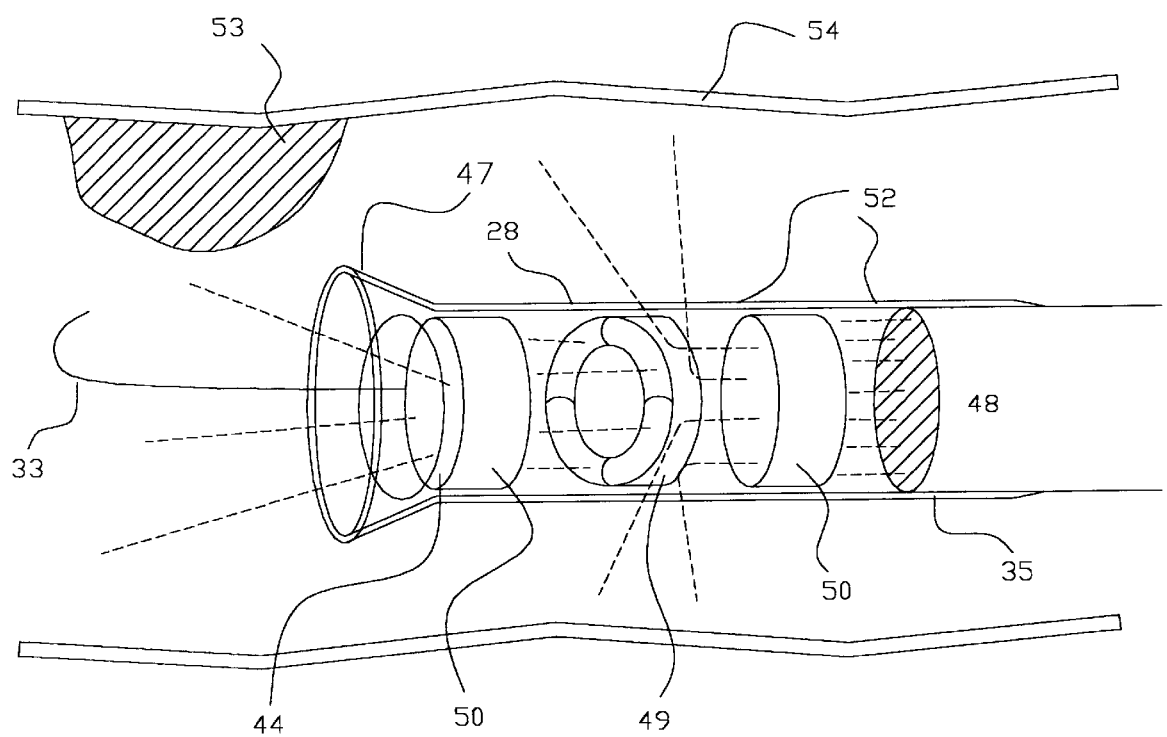
FIG. 11B depicts the distal end of the infrared endoscope system in FIG. 11, inserted in a coronary artery with an athlerosclerotic plaque deposit.

FIGS. 11A and 11B depict the first embodiment. FIG. 11A shows the entire system of a flexible infrared (IR) endoscope whose main components are the laser diode (41), infrared endoscope catheter (25) and the infrared camera (39). The infrared endoscope in this embodiment inspects the interior of a coronary artery to determine the conditions of an athlerosclerotic plaque, before and after an angioplasty procedure. Since a typical coronary artery has a diameter of 3 millimeters, a 1–1.5 millimeter diameter infrared endoscope would usually not be further than 2 millimeters from the vessel wall. As seen in the teaching above, wavelengths starting in the 1.5–1.8 micron region are useful in this application; this wavelength visualizes structures at a distance of 4–5 millimeters through blood. A wavelength of 1.7 microns is chosen since it corresponds to a water absorption local minimum (FIG. 2). The higher wavelength regions may also be used in this application. In particularly, the region centered at 2.1 microns would also be highly suitable for this embodiment. This region permit viewing arterial structures about 10 millimeters through blood. The higher wavelength regions (3.8–4.4, 4.7–5.3 and 7–10) would provide clearer images, but would likely employ larger optical fibers—making the infrared endoscope catheter stiffer. Larger fibers make the catheter stiffer and more difficult to maneuver in the tortuous coronary arteries.

Referring to FIG. 11A, after the light reflected from the coronary artery structure is collected through an optical head assembly (46) and transmitted up the fiber optic cable past a beamsplitter (24), through camera optics (37), to the infrared camera (39) where it is detected by the infrared camera sensor (38) and converted to an electronic signal. This signal is relayed down the camera cable (36) to the image processing unit (35). This unit uses known image processing techniques to enhance the image created by the reflected and scattering light—providing a more distinct view of the arterial lumen. The image-processing unit is connected with electrical cables to the central processing unit or CPU (29) which reconfigures the signals and transmits these signals through an electrical cable (34) to the video processor (32) which processes the suitable for video imaging. Connected to the video processor (32) is the video console (30) and a video recorder (31).

In this application, the infrared endoscope (43), with a stylet hole (44) on the side of the catheter (monorail configuration) is slid over a guide wire (45), which has been placed through the site of athlerosclerotic plaque undergoing an angioplasty procedure. The infrared endoscope is configured for side- and forward viewing to permit imaging the arterial lumen as well as a region ahead of the catheter. Each view will be presented separately or in a combined image on the video console (32). The side view will be most useful in providing detailed images of the coronary artery lumen at the plaque site. This view will permit the shape and nature (calcified or fatty) of the plaque to be determined, prior to angioplasty. Furthermore, the lumen of the deployed stent can be accurately characterized. Observation of stent buckling would suggest insertion of another angioplasty catheter to either apply more pressure to straighten the buckle, or insertion of an additional stent overlapping the original stent. The forward view would prove useful in catheter navigation through the vascular tree to the coronary artery containing the athlerosclerotic plaque deposit.

In this embodiment, a 1.7-micron-wavelength laser diode (41) light source is employed to illuminate the area of interest. This light source passes through a polarization filter

(49) into the fiber optic cable. As mentioned above, each of the polarizations has an effective index of refraction. The particular polarization components or combination of components with the smallest refractive index through red blood cells will suffer less scattering and "see" longer distances. As seen in Equations 12, 13, scattering cross-section—and therefore viewing distance—is proportional to the refractive index difference $\delta$. Accordingly, the polarization filter is designed to create the lowest index of refraction light beam through red blood cells.

In this embodiment, a 1.7-micron wavelength laser diode (41) light source is employed to illuminate the area of interest. This light source passes through an optional polarization filter (49) into the fiber optic cable. The use of polarized light could have several impacts on objects illuminated. The two components of polarized light, the s and p orientations, can have different indices of refraction in organic media as well as angles of incident at the object of interest. The differences in the index of refraction will cause either more scattering or less scattering, as the case for lower index of refraction. It is possible that other polarization states, such as elliptical or circular can be used for a better match to transmit through the media because of its optical properties. As seen in Equations 12 and 13, the scattering cross-section and therefore viewing distance is proportional to the refractive index difference $\delta$. Accordingly, the polarization filter is designed to create the lowest index of refraction light beam through red blood cells.

The infrared endoscope could image the plaque deposit from a forward-view—aiding in navigation of the vascular tree. With this wavelength, a cross-section approximately 4–5 millimeters, ahead of the infrared endoscope catheter, could be imaged. This permits navigation of smaller coronary arteries. Small coronary artery branches, not previously navigable with radiographic dye imaging techniques, could be identified and entered. When the lumens of some of these branches are reduced, deleterious cardiac consequences often occur. Prime examples are the coronary arteries (about one-millimeter in diameter) which supply blood to the natural pacemaker centers of the heart: the atrio-ventricular (AV) and sino-atrial (SA). These nodes control the rhythm of the atria and ventricles respectively. Disruption of blood supply of these arteries leads to rhythm disturbances such as slowdown or long pauses between heartbeats. These conditions are presently treated with a permanently implantable pacemaker—providing a minimum artificial rhythm for the patient. Using this infrared endoscope embodiment, these arteries could be identified and entered with the guide wire over which a small angioplasty catheter could be inserted to apply pressure, and possibly deploying a small stent to re-vascularize these arteries. In addition to navigation, the athlerosclerotic plaque deposit could be visualized—without inserting the catheter through the plaque deposit. This would be important in visualizing plaque deposits that leave a lumen too small for passage of a catheter. This would permit smaller sized catheters to be inserted to apply angioplasty or plaque debulking procedures (atherectomy procedure).

In these current procedures, a guide wire is first inserted in the vasculature near the groin area and threaded, under flouroscopic guidance, to the target coronary artery branch. Once the plaque site is reached, the guide wire is advanced beyond the plaque, which only partially blocks the artery. Over the guide wire, an angioplasty catheter is inserted and threaded through the vasculature to the plaque site. The angioplasty catheter contains a liquid-filled, expandable balloon and usually a stent; a metallic tube that assumes a permanent, expandable shape. Once the balloon portion of the catheter is at the plaque site, the balloon is expanded with pressurized saline solution, leaving the stent permanently extended and the artery lumen open. It is desirable to see the athlerosclerotic plaque before and after angioplasty so that the increased opening of the artery can be quantified, and the improvement in blood flow can be accessed. To this end, the over-the-guide wire infrared endoscope would be inserted, prior to angioplasty catheter insertion, to visualize the lumen at the site of the plaque. After angioplasty catheter insertion, the lumen and stent deployment will again be visualized. It has been shown that the 10–20% restenosis incidence (reforming of blockage) is often due to improper stent deployment or improper positioning of the stent.

Again referring to FIG. 11A, the infrared endoscope components are shown in summary form. An infrared endoscope is constructed of the same three component areas as the conventional visible-region endoscope: the optical head (46), fiber optic cable (48), and the infrared camera (39) and related components. An additional component, unique to the infrared endoscope catheter is a specifically designed hood (47) that attaches to the front of the catheter for enhanced viewing. The hood (47) transmits the infrared illumination in a more efficient manner through a scattering media, and collects the scattered and reflected infrared light to form higher-contrast images than without a hood.

A more detailed review of the optical head's components and function is shown in FIG. 11B. This figure shows the distal end of the infrared endoscope catheter (43, FIG. 11A) in a coronary artery bounded by the arterial wall (54), and in close proximity to a plaque deposit (53) extending from the arterial wall (54). The head has the following major components: focusing lenses (50) and optional gradient index lens assembly (49), illumination fiber's interface and interface between the imaging optics assembly (52) and the transfer fiber optic cable (48). The imaging optics (50) collects the reflected light from areas or objects that are illuminated along the periphery of the artery walls or the volume forward of the IR catheter, and forms an image of this space on the fiber optic transfer cable (48). The hood (47) can alter the peripheral field-of-view of the optical head. A hood can concentrate the illumination and the limit the field-of-view to a narrow angular segment of the 360-degree perimeter if desired. The imaging optical assembly can consist of discrete optical lenses that are designed specifically for the field-of-view, F/#, and wavelength regions of interest, or the use of a gradient index lenses (49) as shown that have similar optical parameters. Either or both of these optical collection techniques can be used in the design of the IR optical heads. For example, a gradient fiber lens (49) may have the F/# and field-of-view parameters of interest, but the quality or resolution of the image may not be sufficient, so an additional optical lens may be added in front or behind the gradient fiber lens to improve this requirement.

The fiber optic transfer cable (48) performs two functions: it transfers the optical image from the head assembly to the IR camera and carries the illumination fibers that provide light for viewing. The fiber optic components can be manufactured from optical glass or fused silica. Both of these materials are commonly used in the manufacturing industry for optical fibers. It is possible for the optical fibers to be doped with other chemicals to enhance the transmission of particular IR wavelengths, similar to processes performed for the communication fiber cables. This doping process is only anticipated if the additional transmission is needed. The illumination method used in this embodiment is useful when small outer diameter is required, this technique is coaxial illumination. The coaxial illumination method does not require separate illumination fibers to be present in the fiber optic transfer cable.

Referring to FIG. 11A, the illumination is transferred directly into the imaging optical fibers prior to the optical relay assembly by means of an optical beamsplitter (24). An optical beamsplitter allows two separate optical paths to be combined as one. The two optical paths are the IR illumination and the entrance of the IR imaging fiber optic cable assembly. After the beamsplitter folds the IR illumination into the fiber optic assembly, the illumination and the imaging optical paths travel in the same fibers, but in opposite directions. When the illumination energy reaches the other end of the fiber optic cable prior to the optical head, it will exit the fibers with the same NA it entered at the opposite end. The optical head's imaging optics will project the illumination into a solid cone of light determined by the focal length of the optical elements.

The direction of the cone of illumination from each fiber can be influenced by mechanical positioning and pointing the fiber ends in a direction other than straight-ahead parallel to the optical head's optical axis. This positioning of the fibers can produce a variety of illumination patterns. One other technique to influence the projected direction of the cone of light from each fiber is to polish a facet or a prismatic shape on the end of the fiber. This shape can cause an abrupt change in direction of the projected light that is related to the angle of the facet. Several potential uses of the facetted fibers would be to arrange them with some non-facetted fibers to aid in eliminating some of the dark cone associated with the non-facetted fibers. The other use of the facetted faces on the fibers would be to direct their light cone all inward around the face of the optical head or all outward away from the face of the optical head. This would permit concentration of the illumination in either of these directions.

TAN (A/2)=1 mm/Focal length, where A is the projected angle of illumination,

A=53.13 degrees in this case.

An advantage of the above-described coaxial illumination technique is to eliminate the illumination optical fibers in the fiber optic transfer cable; this allows the cable assembly to have a smaller mechanical diameter than in an embodiment having separate illumination and imaging fibers, as discussed in an embodiment below. The possible disadvantage to the coaxial illumination method is if some of the illumination can scatter back into the field of view of the IR camera, it will appear as random noise in the video image. Random noise will reduce the overall image contrast. In order to reduce the amount of scattered light caused by the beamsplitter (24) and the end of the optical fiber assembly, the optical surfaces need to be carefully polished so as to eliminate the majority of the surface defects, and have these optical surfaces properly coated with anti-reflection film. In addition to these precautions, the imaging processing is programmed to reduce the intensity of stray light not associated with the image features.

SECOND EMBODIMENT
Intra-Heart Chamber Application

The second embodiment is for at infrared endoscope placed in the right atrium chamber of the heart during a catheter ablation procedure to visualize the location of the catheters, anatomical markers and the location of radio frequency or laser-induced burns. Catheters are placed in the right atrium by first dilating a vein in the neck, groin or leg regions, gradually dilating the vein with a series of larger sized needles, and eventually inserting a hollow tube—called a lead introducer. Catheters can also be placed in the left atrium or ventricle by entering the patient's arterial system. For right atrial application, the lead introducer is threaded through a vein in the vasculature to their exit point in the right atrium. The veins positioned at the the top and bottom of the right atrium are called the superior and inferior vena cava, respectively. The lead introducer is extended through the inferior or superior vena cava—providing an in-dwelling tube to the right atrium. Once the lead introducer is in place, catheters can be placed in the introducer and easily threaded in the atrium.

Since the anatomy of the heart is larger, after the catheter is introduced, a mechanism is needed to steer the catheter to different places in the heart. Traditionally, steering has been accomplished by inserting a guide-wire in the center of the catheter. If a change of position is needed, the guide-wire is withdrawn, reshaped and re-inserted in the catheter to change its overall orientation. In the infrared endoscope, a similar steering mechanism is used with a side stylet (monorail) configuration so that the integrity of the optical fiber is not breached. The stylet can be withdrawn, re-shaped and re-inserted into the lead introducer. Several pre-shaped stylets will be available. These stylets will permit easy entry into various parts of the cardiac anatomy. More sophisticated steering mechanisms—such as those employed in some heart catheters and conventional, visible-light endoscopes could be used in lieu of the removable stylet approach used in this embodiment.

The region in the lower right atrium, bounded by the tricuspid valve and the os of the coronary sinus is frequently analyzed to ascertain sub-areas, which have earlier cardiac activation. Once identified, they are ablated using radio frequency or laser energy. This region is so small, no imaging techniques exist today to view this region. Exploration is guided by the electrical activation patterns measured from electrophysiologic catheters in the right atrium. An infrared endoscope would greatly guide this procedure. By imaging this region with the infrared endoscope, the precise location of the ablation catheter location could be determined relative to anatomical markers. More importantly, the location of the burns could be visualized; guiding the placement of additional burns. For example, burns could be connected—improving the chances of ablating the offending cardiac fiber responsible for the arrhythmia. This technique applied to the atrial wall is critical for the eradication of atrial fibrillation. A series of connected burns would isolate segments of the atrium from adjacent segment—a catheter version of the Maze open-heart surgical procedure.

A longer wavelength is required to produce a viewing distance of about 10 millimeters. The specific wavelength of 2.1 microns is chosen since in it corresponds to a local minimum in water absorption (FIG. 2). This wavelength allows viewing cardiovascular structures, through blood, at distances of about 10 millimeters. Since water absorption is higher for this wavelength, a higher wattage laser diode is used. In this case, a pulsed laser diode is used with an output light intensity in the order of one watt. The exact wattage required depends on the reduction in absorption extinction coefficient for blood. The approximate one watt estimate is based on the water absorption extinction coefficient value at a 2.1 micron wavelength.

A 10-millimeter distance is sufficient to view the placement of nearby electrophysiologic or ablation catheters. Adjustment of the focal length in the optical elements will project the light beam traveling down the fiber optic cable into a solid cone with wide angles (for example 45–75 degree angle). If 60 degrees were chosen, the infrared endoscope, 10 millimeters from the valve plane, would illuminate a circular spot on the plane about 30 square millimeters in area. Anatomically, this corresponds to a length, from the edge of the orifice of the tricuspid valve, past the os of the coronary sinus, extending to part of the septal wall in the right atrium—the region usually of interest in accessory pathway ablation. Repositioning the infrared endoscope in four different locations around the tricuspid valve is sufficient to view the entire tricuspid valve plane.

Other applications or procedures where the second embodiment can be used include cardiac valve inspection (natural and artificial), viewing septal defects, myocardial infarctions and transpositions of the heart, viewing in-dwelling catheters and providing navigation guidance for catheters. Guiding electrode placement in catheters could also be realized with the infrared endoscope in, for example, pacing and defibrillator electrodes. Guidance of channels made in the heart during transmyocardial revascularizaion procedures would also be realized with the infrared endoscope.

Besides the accessory pathway ablation presented in this embodiment, guidance of many other ablation procedures would be beneficial. In the above-mentioned procedure for eradication of atrial fibrillation, connected burns, shaped as lines, need to be made along the length of the atrium. The infrared endoscope in this embodiment could visualize the length of the atrium in 4–5 positionings of the infrared endoscope catheter. In the ventricle, viewing the myocardial infarction through blood, in patients, with post-myocardial-infarction ventricular tachycardia, would allow burns to be placed around the periphery of the infarct—possibly eliminating the tachycardia. In these applications, or others not mentioned, the field-of-view of the optics can be increased easily from that normally used in this or the first embodiment by decreasing the focal length of the optical elements. The extent of the increase is only limited to the forward imaging range of the optical assembly.

The optical system for this application (FIG. 12A, B) can use many of the same components as the first embodiment. As in the first embodiment, a variety of light sources are candidates at this wavelength, including laser diodes light emitting diodes, lasers and filtered incandescent light sources. In this embodiment, a laser diode (71) emitting approximate watt-sized pulses at a 2.1-micron wavelength, is used as the light source. As in the first embodiment, this light is passed through a polarization filter constructed to pass the lowest refractive index light for red blood cells. Separate imaging and illumination fibers are used in this embodiment.

Figure 12A:
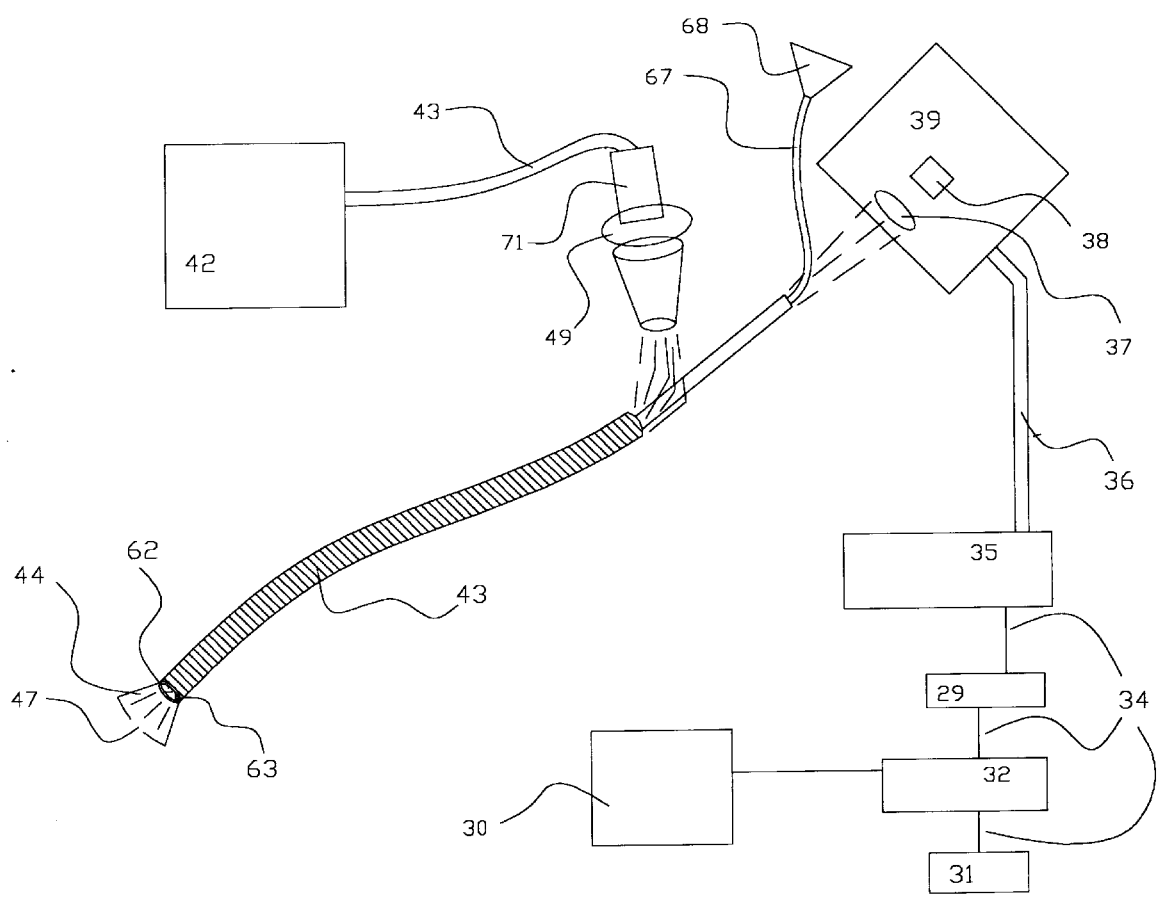
FIG. 12A depicts the infrared endoscope system for intra-cardiac application.
Figure 12B:
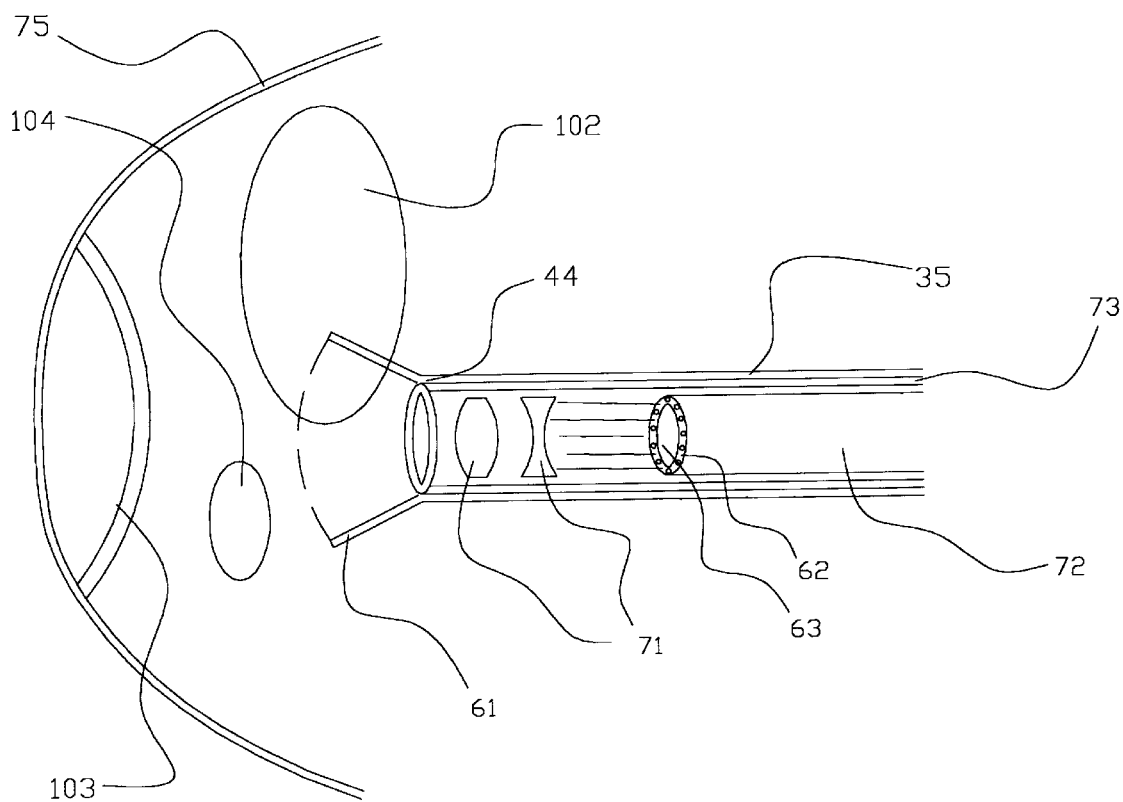
FIG. 12B depicts the distal end of the infrared endoscope system in FIG. 12A inserted at the base of the right atrium near the tricuspid valve.

Another difference in the second embodiment is the use of separate imaging and illuminating fibers instead of the beamsplitter. Referring to FIG. 12B, the laser diode (71) is connected to the illumination fibers (73) which are placed on the periphery of the catheter. An efficient light connection is made with the illumination fiber ends (62) and transmitted sown the illumination fibers (73) where the light is transmitted to the optical hood (61), which helps concentrate the light before the light enters the bloody environment. The light is scattered and reflected by the cardiovascular surfaces under visualization. Reflected light passes through the transparent cap (44), into the collection optics (71) and into the collection fibers ends (63) and out to the cardiac surfaces. The infrared endoscope contains an outer sheath of flexible housing (35) and transparent cap (44) to prevent blood intrusion into the interior of the catheter.

Referring to FIG. 12B, initially a different IR camera (34) preferably is used, because commercially the ideal camera for both embodiments is not beleived to be available. It is anticipated that an IR sensor area will be manufactured that will cover the wavelength range of both applications. The optical materials for the imaging lenses (46) and illumination fibers (73) and collection fibers (63) are the same as in the first embodiment, but if additional transmission is needed, then specific infrared materials can be used. At this wavelength, light transmission can be enhanced using special materials especially transmissive in the infrared region. The specific materials for the imaging optical elements could include infrared grade materials from Schott Optical, O'Hara Optical, Corning Glass, or several infrared material suppliers. These materials can include optical grade silicon, sapphire, fused silica, zinc sulfide, zinc selenide, and a variety of crystal materials used in the IR imaging industry.

Since this embodiment is for use in the heart, it supports the use of larger diameter fiber cable assemblies, which means the collection optics can be larger if needed. Catheters with an outer diameter of 3–5 mm are routinely placed in the heart. Referring to FIG. 12A, the imaging or coherent fibers will be a collated bundle of very small diameter fibers, arranged such that the image from the optical head is exactly transferred to the other end. The material selected for these coherent fibers will be maximum transmission for the wavelengths in use. The same material selection applies for the illumination fibers, except their diameter does not have to be as small. To successfully transfer the image from the coherent fiber bundle end to the IR camera's sensor it is necessary to use an optical relay lens. The relay lens will re-image and change the image size or magnification to match the camera's sensor array. This relay lens will be mechanically mounted to the IR camera, will have an interface to attach the fiber cable.

The grouping or configuration of the illumination fibers at the optical could depend on how close or the proximity the optical head will be used to observe an area or object of interest. For example, an illumination configuration of the fibers around the perimeter of the optical head, circular configurations, is better used when the object of interest is at least 34 mm in front of the optical head. The circular configuration with the fiber ends pointed forward produces a darkened interior cone where very little scattered illumination reaches, and makes viewing areas or objects inside the 3–4 mm distance harder to view than outside the 4 mm space. The dark cone region is a result of how the light is projected from the ends of the fibers. Fibers do not project light into a hemispherical pattern; their projection pattern is limited to the numerical aperture (NA) of the fiber. Typical NA's of fibers vary from 30–80 degrees, giving the dark cone region an angular shape of 30 to 80 degree included angle. It is understood that the larger the NA of the fibers the shorter the length of the darken cone of minimal The illumination fiber's termination near the IR camera (39) is where the fibers are gathered in a small round bundle and exposed to the proper light source for the wavelengths employed. The termination at the other end of the transfer cable will interface efficiently with the optical head, so there is little or no light lost in the transfer. The arrangement or configuration of the illumination fibers in the optical head can vary depending on the illumination pattern or condition desired for a particular investigation. In this application, the perimeter or side view is more useful along with the forward view so the fibers will be arranged and polished so that the light pattern is directed out to the sides of the optical head. The same is true of the forward view; fibers would be positioned so that more light is projected forward than out to the sides or perimeter. The hood (47) has an influence on the distribution and direction of the projected illumination.

FIG. 12B shows the distal end of the infrared endoscope (FIG. 12A, 43) placed in the bottom of the right atrium, passed from the superior vena cava vein. The infrared endoscope catheter is near the os of the coronary sinus (104), the inferior vena cava (102) and the tricuspid valve (103). Electrophysiogic and ablation catheters are placed in this region for the purpose of mapping activiation patterns and burning a spot(s) in a critical location to disrupt the arrhythmia. Visualization of the catheter ends, electrode placement and the burn location is accomplished with the infrared endoscope. The illumination fibers (73) terminate at the illumination fiber ends which are focused through an infrared transparent cap (44) into the bloody environment and the hood (61) to illuminate a surface area of about 30 centimeters. The reflected and scattering light pass through the catheter end to the collection optics (71) and focused to the collection fiber ends (63) to the infrared camera (FIG. 12A, 39).

The larger outer diameter assembly can use a larger outer diameter imaging fiber optic cable. The larger cable for a given field-of-view will provide more resolution. The higher resolution at the fiber cable is due to more small, outer diameter fibers in the imaging bundle, and less magnification has to be used with the optical relay. If the larger optical apertures are not needed then the possibility of other attachments or tools could be included in the larger outer diameter for the assembly. The tools could be specifically designed instruments that surgeons could use during their examination or repair while viewing the tricuspid valve plane or other areas of the heart. These tools would include staplers, radio frequency electrodes, and lasers as well. The method of illumination is the same as the first embodiment except for the wavelength (2.1 microns) of the light source.

THIRD EMBODIMENT
Lead Introducer Application

In the third embodiment, the infrared light is placed around the periphery of a lead introducer. In typical heart catheter procedures, a tubular element, called a lead introducer, is threaded down the vasculature and inserted to an entry point in the heart—the orifice of the superior or inferior vena cava in the right atrium. Once positioned, catheters can be inserted in the lead introducer and positioned in various places in the heart. Present-day lead introducers have no visualization capability. In this embodiment, the fiber optic cable is placed in an annular-tube configuration around the outside of the lead introducer. It is appreciated that a similar construction technique could be employed around the periphery of any catheter, such as an angioplasty, ablation or pacing catheter.

Light sources operating with a wavelength centered in the 2.1 or 4.0-micron region are suitable for this application. At a 2.1-micron wavelength, objects can be imaged through about 10 millimeter of intervening blood with light sources in the watt-region. At a 4.0 micron wavelength, viewing, from a scattering view, is very long. At a 4.0-micron wavelength, from a scattering perspective, considerably longer distances can be viewed through blood; this wavelength, predict viewing distances through blood at distances exceeding several centimeters. According to FIG. 9, a 4.0-micron wavelength has a normalized scattering cross-section of 0.295; equivalent to about a 10:1 water dilution. The 4.0-micron wavelength is chosen to illustrate the design of higher wavelength systems.

Consequently, a major difference, in this embodiment, is the need for a high-wattage light source due to the increased absorption extinction coefficient at this wavelength. Inspecting the water absorption curve (FIG. 2), the local minima for free water occurs at about 4.0 microns and is many times larger than the local minima at 2.1 microns; suggesting the corresponding unknown curve for blood would show a similar increase. Careful examination of the microstructure of the absorption extinction coefficient of blood will reveal the lowest absorptive wavelength for the region centered around 4 microns. Using mass spectrometry equipment, the region from about 3.9–4.1 will be surveyed in fine detail. From this data, the lowest absorption wavelength can be determined.

Depending on the actual absorption found and the sensitivity of the infrared camera, a light source in the kilowatt region is needed to shine through distances in the centimeter-region. Because of the exponential fall-off of transmission as a function of distance (Equation 2), high wattage will be required to see these distance extremes.

Very high wattage can be used without causing tissue damage if the light source is flashed; allowing tissue cooling prior to the next flash. In this embodiment, the light source would be flashed for about 5 microseconds each heart beat; with a corresponding ratio on/off time (duty cycle) of about 1:500,000. This pulse duration and duty cycle allow the use of light sources of hundreds of kilowatts. The wattage is dictated by many variables including: actual minimum blood absorption value, distance to be viewed, camera sensitivity and practical considerations such as cost and size of the device.

The timing of the 5-microsecond pulse will be synchronous with the heart so that each flash catches the heart in the approximate same position. In this case, pictures refreshed at one frame per heartbeat would not appear to jump or move. The ideal point for the flash is when the heart is quiescent; a period called diastole. From initiation of the electrical impulse, which can be measured from the ECG recorded on the patient's skin, or alternatively, within the patient's heart with metallic electrodes. Following the electrical impulse, the heart contracts (systole) between 0.1–0.3 seconds later; diastole occurs between about 0.3–0.8 seconds. A light flash in this period would be the most desirable to minimize picture jitter. Since the embodiment is a lead introducer, it is easy to record the ECG internally by having an electrode(s) on the introducer; additionally, this technique provides for more precise timing of the heart.

Figure 13:
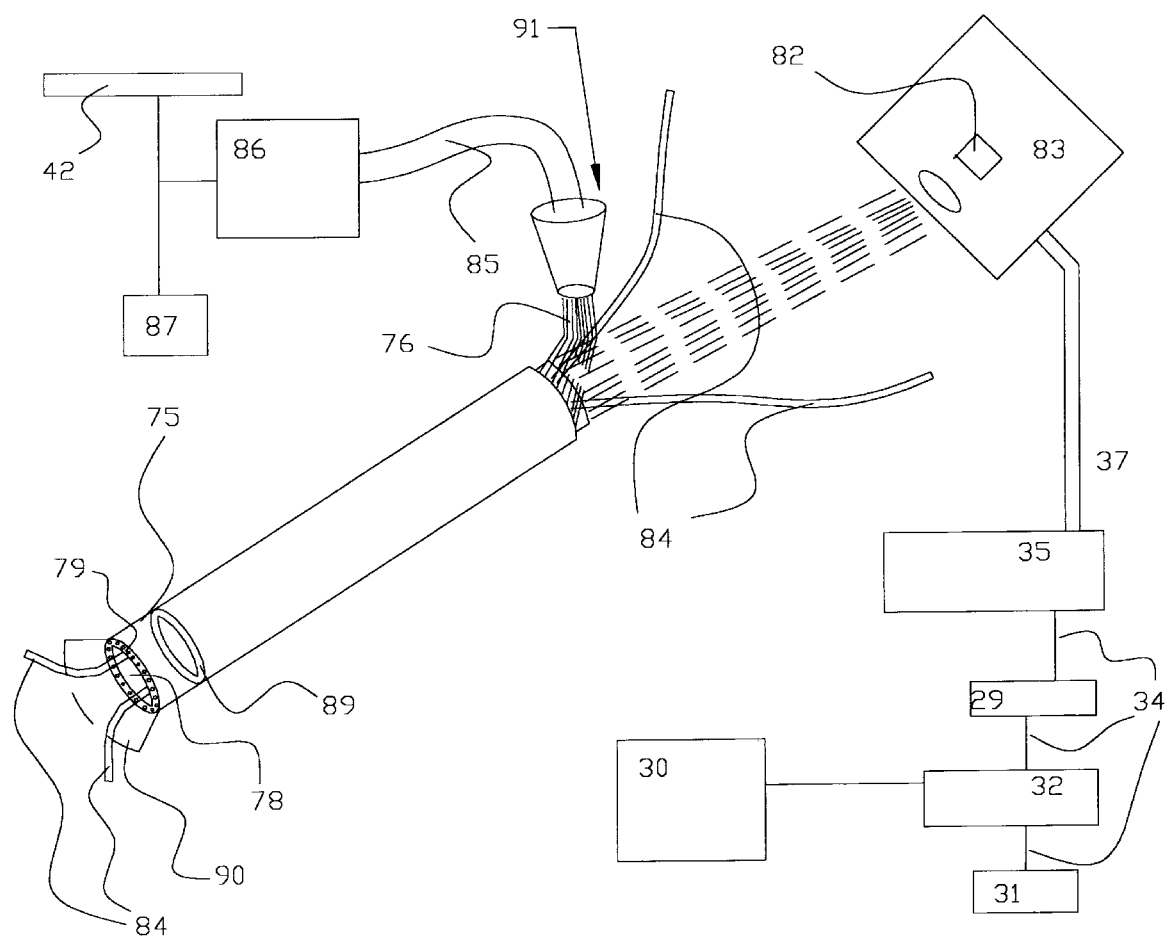
FIG. 13 depicts an infrared endoscope incorporated into a lead introducer.

In FIG. 13, a laser operating with a wavelength of 4.0 microns (86) is triggered by the patient's ECG (87) to fire a 5-microsecond laser pulse at a time(s) during diastole. This pulse is conducted through a light source fiber-optic (85) to the light-fiber optic connector (91). Both of these elements must be transmissive to infrared light at 4.0 microns. The light-fiber optic connector (91) connects to the illumination fibers (76) emanating from the lead introducer. The illumination fibers terminate (78) into the hood (90), which concentrates the illumination.

This embodiment illustrates another arrangement of illumination and collection fibers: the side-by-side approach. In this approach, these fibers each form a half-circumference around the lead introducer. At the distal end of the catheter, the illumination fiber ends (78) are seen to occupy about one-third the circumference of the lead introducer. The collection fiber ends (79) occupy the remaining two-thirds. [I don't see this reflected in the drawings]. When catheters (84) are placed in the field of view, they will be visualized along with the internal surface of the heart.

Reflected and scattering light, guided by the hood (90), enters into the toroidal transparent cap (75), through the torroidal collection optics (89) to the collection fiber ends (78) where they are routed to the sensor (82) of the mid-infrared camera (83). The sensor element (82) is sensitive to wavelengths in the 4.0-micron region. The camera signal is fed through the camera cable (37) to the image processing unit (35) and then the CPU (29). The CPU (29) directs the signal to the video processor (32) and to the video console (30) or video processor (31).

FOURTH EMBODIMENT
OPHTHALMIC APPLICATION

A condition where there has been a rupture of one or more blood vessels supplying blood to the retina can cause temporary loss of sight for the patient. When this condition of mixing the humorous liquid inside the eye with blood occurs it becomes nearly impossible to examine the damage without an operative procedure. The blood-humorous mixture absorbs and scatters all the visible light used in an optical examination of the environment. Without a visual inspection of the problem, an invasive procedure would be necessary to inspect the damage and affect a repair.

An optical instrument similar to a video microscope with a light source, that uses the infrared cameras described in the above text, can be used for external inspection tool. The optical principles allowing allow scattering optical path described in the above teachings can be applied equallyin this application. The infrared microscopic instrument will introduce a small beam of infrared illumination through the pupil, and the optical objective, situated in close proximity will receive the scattered and reflected light from the interior structure of the eye. The infrared microscopic instrument has a variable field-of-view from the wide to the narrow, to allow a broad general view or zoomed in to a narrower more specific field of investigation.

To assure optimal viewing or light collection at the instrument's objective an interface other than air may be required. Interfaces involving intimate contact (no air) or a liquid or optical gel environment could be used to affect the best transfer of light going in and out of the pupil. The optimal optical conditions for light transfer and good signal to noise conditions would suggest either intimate contact or the liquid interface. Both of these interfaces will produce the minimal of optical reflection at the pupil. The optics for Fresnel reflection at this interface will cause a small percentage of the incoming illumination to be reflected back into the instrument's objective. This small reflection of energy will be directed back to the infrared camera's sensor, and appear as optical noise in the overall image. To minimize this reflection will improve the overall signal to noise ratio of the instrument.

Potential light sources for this instrument are the same as discussed in the above text, filtered incandescent, LED's and laser diodes. The uses of different polarizations of the transmitted and received illumination are also applicable. As in most optical environments where liquids and suspended particles are present, certain states of polarized light pass through the medium with less scattering, The choice to use polarized or non-polarized light will probably be made by the users of the equipment, after they have examined the injury. The choices of how the entering illumination will pass through the pupil are three. The coaxial illumination technique described in the above text, where the illumination is introduced through a beamsplitter to share the same optical path as the imaging path. The second method is the illumination fibers around the outside of the objective, similar to the optical head in the IR endoscope. The third is a direct injection of a small beam of illumination from the side of the objective, or through a beamsplitter between the objective and the pupil. The third technique may have some mechanical complications and may not be as practical as the first two methods. In the second method, where the illumination fibers provide the light, an optical hood or attachment could be used if special direction or focusing of the illumination is needed. It is possible that an active control of the direction and focusing of the illumination will be needed for a through examination of the damaged area. In this instance, an optical hood or attachment that is independent of the imaging path of the microscopic instrument is needed.

Figure 14:
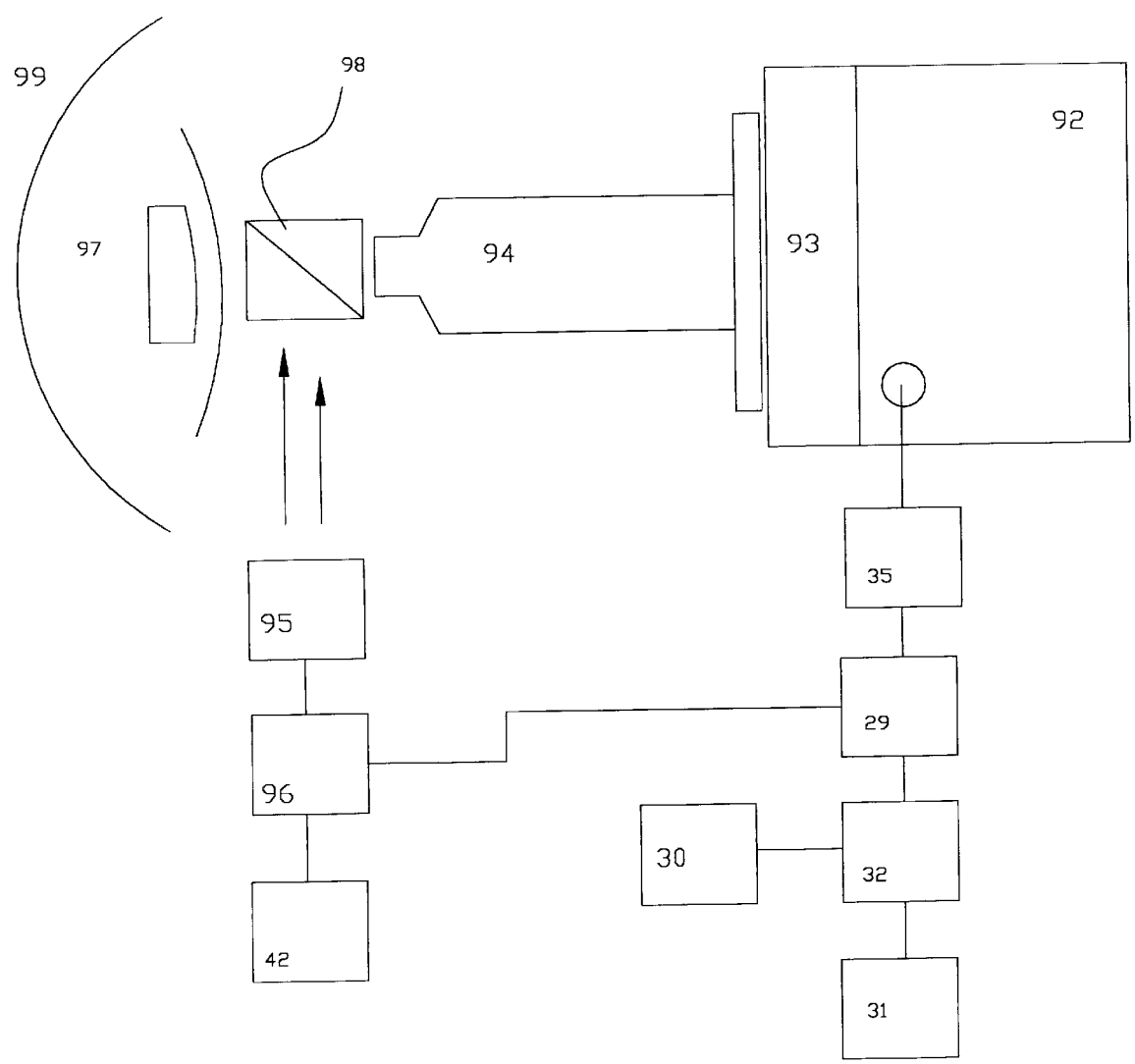
FIG. 14 depicts an infrared endoscope system suitable for illuminating the eye.

A typical parameter setup for the IR examination, using the beamsplitter technique (coaxial illumination) would be as shown in FIG. 14 without the beamsplitter device (98) located near the eye (99). The IR zoom lens (94) would control the cone of illumination exiting the front aperture, and would be either in contact or close proximity to the entrance pupil of the eye (99). The cone of illumination would expand or contract to match the field-of-view of the zoom lens. This feature of matching the illumination cone with the field-of-view of the zoom lens ensures that objects viewed by the IR camera are always under full or nearly full illumination. To tip or tilt the optical axis or centerline of examination for the IR instrument to enable the user "zoom in" on areas of interest other than the central portions of the retina, the device has two options. The first, and least complicated mechanically is to simply move the instrument on a spherical plane that is concentric to a point near the middle of the eye cavity. This motion will assure that the line of sight or centerline of the optics is always directed through the center of the eye's pupil. The practical mechanical freedom of angular centerlines to view into the eye's interior is a cone of approximately 160 degrees. The physical size of the IR zoom lens exit aperture and when it would make contact with the exterior surface of the eye would determine the angle of view entering the eye's pupil. The second method is a optical technique using a pair of rotating optical prisms that redirect the optical centerline without moving the IR lens position with respect to the eye's pupil.

The field-of-view range of the IR zoom lens would be 10–90 degrees, the 10 degrees would represent about 4 mm circle on the retina, and the 90 degrees would contain nearly the whole interior of the eye. If any additional zoom range is needed attachments can be added to reduce the lower end of the zoom range. The controls for the zoom and focus functions are maintained on the interior of the mechanical structure of the lens housing, and extend back to the camera interface. Inside the IR camera structure (92), all control functions of the lens and light source are mechanically interfaced and manipulated via the CPU (29) control panel. This signal is routed to the video processor (32), which in turn feeds the video monitor (50) or the VCR (31).

Since the eye has a depth of about a centimeter, the lowest wavelength found in the 2.0 would be most suitable for this application. Since the suspended particles of blood in the aqueous humour are at a lower density than in whole blood, a light source in the 2.1 microns region is employed. The light source is connected with the gel or air interface to the beamsplitter (98). Unlike the previous embodiments, light does not travel down a fiber bundle, but is instead placed in close proximity to the eye. Since light does not need to be bent in this application there are no fibers in the collection component of the system as well. Light exits the lens (97) and illuminates the interior of the eye (99). Reflected and scattering light is collected by the infrared zoom lens (94) and transmitted to the infrared camera (92).

The methods and embodiments above describe an infrared endoscope useful for imaging structures through blood. The parameters of blood (dimension of particle, number of particles, refractive index difference and the absorption of the media) determine the wavelengths that the red blood cells can be "seen through". In the more general case of a fluid made opaque by the presence of suspended particles, the particular parameters can be substituted in the normalized cross-section scattering equation to derive the wavelengths where a considerable reduction in total normalized scattering cross-section would be expected. These wavelengths would have longer viewing distances; structures could be imaged through the media. While it appears that blood is the principle application, there may be industrial applications where viewing through fluids made opaque by suspended particles is useful. The media may be aqueous or another fluid. Since water is one of the few liquids which exhibits opacity in the infrared, the choice of wavelength would not be mitigated by high absorption. If the fluid is water, than both all scattering and absorption teachings are applicable. Since all body fluids are aqueous in composition and are rendered opaque by biological particles (which always have only marginally higher refractive index), results would be very similar to blood.

In summary, the methods and embodiments disclose the advantage of viewing structures immersed in blood at infrared wavelengths. The infrared wavelengths that allow greater viewing distances were identified based on the size and refractive index of the red blood cell. This methodology developed, can be applied to any liquid with suspended particles if the same parameters are known or measured. We find no references regarding imaging structures through a fluid, rendered opaque by suspended particles, in the patent or technical literature. Methodology has been provided to determine the infrared wavelengths, where viewing distance through the liquid-particle mixture become longer. If overall volume and surface area of the particles is known, Equation 22 can be used to calculate the equivialent radius of the Mie-sphere. The sphere radius and refractive index difference between particle and medium allow calculation of the scattering cross-section versus wavelength. Choosing a wavelength where the Mie scattering cross-section is in the decreasing phase improves viewing distance through the liquid with suspended particles. For a given desired viewing distance, an infrared wavelength can be selected to image structures immersed in such an environment, at that given distance. If the liquid is not water, it will likely be transparent or semi-transparent in the infrared spectrum. If the fluid were not water, these restrictions on wavelength would not apply; instead the viewable distance—through the liquid with suspended particles—would steadily increase with increasing wavelength of the illuminating light source. As higher wavelengths are utilized, the approximation of Equation 19 can be used which demonstrates that scattering cross-section is inversely proportional to the square of the illuminating wavelength.

Viewing distance can be estimated by measuring the distance increase as the liquid-suspended particle mixture is diluted with more of the above liquid. Dilutions, simulate different total scattering cross-sections—predicting the effect of lowering scattering cross-section by illuminating the structure with longer wavelengths. For blood, this cross-section decrease becomes apparent at about 1.4 microns as verified experimentally. In fact, any particle of biological origin immersed in water would have similar characteristics. Since the refractive index is only marginally higher than water, Equations 17 and 18 would apply to the suspension. Determination of particle size and approximating it with a sphere of given radius, determines the scattering cross-section surface area for a given wavelength, using Equation 18.

If the fluid is water there are only bands where water is semi-transparent. Water has only wavelength bands at 1.5–1.8 microns, 2.0–2.4 microns and 3.7–4.3 microns In these regions water is semi-transparent requiring much lower intensity light sources. Additionally, the regions from 4.6–5.4 microns and 7–14 microns are also favorable wavelengths, since local water absorption minima occur in these regions. Relative to neighboring wavelength regions, water has the least opacity for these regions. However, the higher absorption in these regions would require the use of high intensity light sources in perhaps a flash configuration.

For blood, FIG. 10 is a graph showing the overall absorption by water and hemoglobin added according to Equation 2. Note that only the regions around the local minima, designated 1–5 are possible windows to view through blood. These minima may not occur exactly at these values since added constituents affect the precise location of the minima. For example, salt water has the minima at slightly different locations from pure water.

It should be understood that the scientific theories disclosed herein are not essential to the practice of the invention, the utility of which has been demonstrated as a matter of fact. Accordingly, any later discoveries which may cast doubt on any of the theories disclosed herein should not be seen as derogating the disclosed invention. Still, it is believed that the disclosed theories may be useful in appreciating the pioneering scope of the present invention, and may stimulate further research and development in the field. Similarly, it should be understood that the numerical limitations disclosed herein are based upon existing knowledge, and may be subject to revision in the future. Accordingly, such limitations are to be regarded as approximate. After appreciating the fundamental concepts of the present invention, it is well within the skill of the art to develop, for example, more exact absorption data.

Having described the optical principles, methods, techniques, and the necessary mechanical components for an infrared endoscope, we claim the following:

What is claimed is:

1. A method of acquiring an image of a structure obscured in the visible wavelength-region by blood, comprising the steps of:

projecting monochromatic infrared illumination at a wavelength corresponding to a local absorption minima through the blood to the structure to be imaged, such that at least some of said infrared illumination is reflected or scattered by the structure;

collecting at least some of the reflected or scattered infrared illumination at the same wavelength; and transmitting at least some of the collected scattered illumination to an infrared camera, whereby an image of the structure is formed.

2. The method of claim 1, wherein the projecting step includes inserting the infrared light source directly to a position proximate the structure.

3. The method of claim 2, wherein the projecting step includes projecting illumination through an air interface.

4. The method of claim 2, wherein the projecting step includes projecting illumination through a gel interface.

5. The method of claim 1, wherein the projecting step includes inserting a transmission line capable of transmitting infrared illumination to a position proximate the structure.

6. The method of claim 5, wherein the projecting step is accomplished using a transmission line which is a fiber optic cable.

7. The method of claim 5, wherein the projecting step includes inserting the transmission line into a body of a patient.

8. The method of claim 7, wherein the projecting step includes flexibly inserting the transmission line through the vascular system of a patient.

9. The method of claim 1, wherein the projecting step includes projecting illumination having a wavelength greater than 1.4 microns.

10. The method of claim 9, wherein the projecting step includes projecting illumination having a wavelength in a range selected from the group consisting of 1.4 to 1.8 microns, 2.1 to 2.4 microns, 3.7 to 4.3, 4.6 to 5.4, and 7 to 14 microns.

11. The method of claim 10, wherein the projecting step includes projecting illumination having a wavelength in a range selected from the group consisting of 1.4 to 1.8 microns, 2.1 to 2.4 microns and 3.7 to 4.3 microns.

12. The method of claim 11, wherein the projecting step includes projecting illumination having a wavelength in a range selected from the group consisting of 1.4 to 1.8 microns, and 2.1 to 2.4 microns.

13. The method of claim 1, wherein the collecting step utilizes a device positioned proximate an end of said transmission line for concentrating said infrared illumination.

14. The method of claim 13, wherein the collecting step is accomplished using a device which is a hood.

15. The method of claim 14, wherein the collecting step is accomplished using a hood which is flared.

16. The method of claim 1, wherein the projecting step includes transmitting infrared illumination along a first transmission line, and the transmitting step includes transmitting infrared illumination along a second transmission line separate from the first transmission line.

17. The method of claim 16, wherein the projecting step is accomplished such that the first transmission line and second transmission line are fiber optic cables.

18. The method of claim 16, wherein the projecting step is accomplished such that the second transmission line defines a core and the first transmission line is a bundle of fibers positioned around the core.

19. The method of claim 16, wherein the projecting step is accomplished such that the first transmission line and second transmission line are positioned along side each other in a half circular configuration.

20. The method of claim 1, wherein the transmitting step includes transmitting at least some scattered collected illumination through an optical relay lens engaged with the camera.

21. The method of claim 1, wherein the projecting step includes projecting infrared illumination through a fiber and thence through a fiber optic head, the fiber optic head directing illumination in a desired direction with respect to the structure.

22. The method of claim 1, wherein the projecting step includes projecting infrared illumination through a fiber and thence through a fiber optic head having an optical axis, the illumination passing through the optical axis at an angle other than parallel.

23. The method of claim 1, wherein the projecting step includes projecting infrared illumination through a fiber and thence through a fiber optic head, the fiber having a polished faceted end for concentrating said illumination in a desired direction.

24. The method of claim 1, wherein the projecting step and transmitting step are performed on a common transmission line.

25. The method of claim 24, wherein the projecting step and transmitting steps are accomplished using a common transmission line that includes fiber optic cables.

26. The method of claim 25, wherein the projecting step and transmitting step are performed using an optical beamsplitter.

27. The method of claim 1, wherein the projecting step includes projecting polarized illumination.

28. The method of claim 1, wherein the projecting step includes projecting pulsed light.

29. A device for imaging an object within a bloody liquid medium, the device comprising:
   an endoscope catheter including a fiber optic cable suitable for transmitting infrared light, said fiber optic cable having a distal end and a proximal end;
   an infrared light source engaged with the proximal end of said cable, said light source for transmitting monochromatic infrared light at a wavelength corresponding to a local absorption minima;
   an optical head assembly engaged with the distal end of said cable for transmitting infrared illumination from the infrared light source through the bloody liquid medium to the object and for receiving reflected and scattered light from the object and transmitting said reflected light to said cable; and
   a lens and an infrared camera for receiving said reflected and scattered light from said cable at the same wavelength and forming an image of said object.

30. The device of claim 29, wherein the infrared light source produces infrared illumination at a wavelength greater than 1.4 microns.

31. The device of claim 29, wherein the infrared light produces infrared illumination at a wavelength corresponding to a water absorption local minimum.

32. The device of claim 31, wherein the infrared light source produces infrared illumination in the wavelength regions consisting of 1.4 to 1.8 microns, 2.1 to 2.4 microns, 3.7 to 4.3, 4.6 to 5.4, and 7 to 14 microns.

33. The device of claim 32, wherein the infrared light source produces infrared illumination in the wavelength regions consisting of 1.4 to 1.8 microns, 2.1 to 2.4 microns and 3.7 to 4.3 microns.

34. The device of claim 33, wherein the infrared light source produces infrared illumination in the wavelength regions consisting of 1.4 to 1.8 microns and 2.1 to 2.4 microns.

35. The device of claim 29, further comprising an image processor and video processor engaged with the infrared camera for processing the image formed by said infrared camera.

36. The device of claim 29, further comprising a guide wire or stylet for guiding said endoscope catheter to a desired site.

37. The device of claim 29, further comprising a light focusing hood attached to said catheter proximate said optical head assembly.

38. The device of claim 29, wherein at least a portion of the optical head assembly is housed within a transparent window attached to the distal end of the fiber optic cable.

39. The device of claim 29, further comprising a beamsplitter so that the infrared illumination and the reflected and scattered light share a common optical path.

40. The device of claim 29, wherein the fiber optic cable includes illuminating fibers and imaging fibers separate from said illumination fibers;
   the illuminating fibers being engaged with the light source and the optical head, for transmitting light between the light source and the optical head;
   the imaging fibers being engaged with the infrared camera and the optical head, for transmitting light between the infrared camera and the optical head.

41. The device of claim 29, wherein the light source generates light having a wavelength of about 2.1 microns.

42. The device of claim 29, wherein the imaging fibers form a core and the illuminating fibers are arranged around said core.

43. The device of claim 29, wherein the infrared light source generates light having a wavelength of about four microns.

44. The device of claim 29, wherein the infrared light source generates polarized light.

45. The device of claim 29, wherein the infrared light source generates pulsed light in a flash configuration.

46. An imaging device comprising:
  means for directing infrared illumination at a wavelength through blood so that at least some of the infrared illumination will reflect from an object within said blood, thereby generating reflected illumination;
  said illumination being monochromatic and corresponding to a local absorption minima of the blood;
  means for receiving said reflected illumination at the same wavelength; and
  an infrared camera engaged with said receiving means capable of forming an image of the object.

47. A non-invasive method of imaging an object within a closed environment such as an eye that has a mixture of blood and vitreous humor, where the blood has rendered the object opaque in the visible spectrum comprising the steps of:
  introducing monochromatic infrared illumination into the closed environment so that the infrared illumination is reflected and scattered by the environment;
  said monochromatic infrared illumination being at a wavelength corresponding to a local absorption minima of the blood; and
  receiving said reflected and scattered light at the same wavelength with an infrared camera to form an image of the object within the closed environment.

48. The method of claim 47, that uses infrared illumination wavelengths from 1.6 to 12 microns.

49. The method of claim 47, wherein the introducing step introduces infrared illumination through an air-media interface.

50. The method of claim 47, wherein the introducing step introduces the infrared illumination though an interface selected from the group consisting of liquid and gel.

51. The method of claim 47, wherein the introducing step introduces polarized infrared illumination.

52. The method of claim 51, wherein the introducing step introduces pulsed infrared illumination.

53. Apparatus for forming an image within a closed environment containing a liquid or gel wherein blood has rendered the closed environment opaque in the visible spectrum, comprising:
  means for introducing infrared illumination into the closed environment, whereby the illumination is scattered and reflected;
  means for collecting the scattered and reflected illumination to form an image of objects or surface details of the closed environment; and
  whereby said means for introducing illumination introduces monochromatic illumination at a wavelength corresponding to a local absorption minima and the collecting means collects the scattered and reflected illumination at the same wavelength.

54. The apparatus of claim 53, wherein the introducing means introduces infrared illumination having a wavelength of from 1.6 to 12 microns.

55. The apparatus of claim 53, that uses a fixed focal length optical objective to introduce the infrared illumination into the environment, and receive the illumination exiting the environment.

56. The apparatus of claim 53, wherein at least one of the introducing means and collecting means includes a variable focal length or zoom lens.

57. The apparatus of claim 53, further comprising a beamsplitter engaged with the introducing means and the collecting means.

58. The apparatus of claim 53, further comprising a beamsplitter engaged with the introducing means such that the an illumination optical path and an imaging optical path share a common optical element.

59. The apparatus of claim 53, wherein the introducing means introduces illumination from a fiber optic element distributed around a circumference or to one side of an objective lens.

60. The apparatus of claim 53, further comprising a CPU engaged with the collecting means for enhancing the collected illumination.

61. The apparatus of claim 53, wherein the introduced illumination has an intensity and a duty cycle, and further comprising a CPU processing unit that controls the intensity and duty cycle of the introduced illumination.

62. The apparatus of claim 53, further comprising an ophthalmic repair or surgical laser that can be used to affect repairs or procedures of an eye.

* * * * *